United States Patent
Yates et al.

(10) Patent No.: US 8,210,411 B2
(45) Date of Patent: Jul. 3, 2012

(54) MOTOR-DRIVEN SURGICAL CUTTING INSTRUMENT

(75) Inventors: David C. Yates, West Chester, OH (US); Frederick E. Shelton, IV, Hillsboro, OH (US); Bret W. Smith, Kings Mills, OH (US); Brett E. Swensgard, West Chester, OH (US); Ryan J. Laurent, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 502 days.

(21) Appl. No.: 12/235,782

(22) Filed: Sep. 23, 2008

(65) Prior Publication Data

US 2010/0076474 A1  Mar. 25, 2010

(51) Int. Cl.
*A61B 17/068* (2006.01)

(52) U.S. Cl. ........................ 227/175.1; 227/19
(58) Field of Classification Search .............. 227/175.1, 227/176.1, 178.1
See application file for complete search history.

(56) References Cited

U.S. PATENT DOCUMENTS

| | | |
|---|---|---|
| 3,551,987 A | 1/1971 | Wilkinson |
| 4,429,695 A | 2/1984 | Green |
| 4,809,695 A | 3/1989 | Gwathmey et al. |
| 4,844,068 A | 7/1989 | Arata et al. |
| 5,188,111 A | 2/1993 | Yates et al. |
| 5,403,312 A | 4/1995 | Yates et al. |
| 5,405,072 A | 4/1995 | Zlock et al. |
| 5,413,272 A | 5/1995 | Green et al. |
| 5,417,361 A | 5/1995 | Williamson, IV |
| 5,480,089 A | 1/1996 | Blewett |
| 5,482,197 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |

(Continued)

FOREIGN PATENT DOCUMENTS

CA   2458946 A1   3/2003
(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Lindsay Low
*Assistant Examiner* — Andrew M Tecco

(57) ABSTRACT

A motor-driven surgical cutting and fastening instrument that comprises an end effector, a shaft connected to the end effector, and handle connected to the shaft. The end effector may comprise a cutting instrument that, when actuated, longitudinally traverses the end effector to cut tissue clamped in the end effector. The handle may comprise an electric motor for actuating the cutting instrument and a motor control circuit for controlling the motor. The motor control circuit may comprise a power source connected to the motor for electrically powering the motor and a current control circuit, connected to the power source, for varying the current supplied to the motor from the power source. The current control circuit may vary the current supplied to the motor, and consequently, the output torque supplied by the motor, such that the motor has at least (i) a first, low power operational mode for a first portion of a cutting stroke cycle of the cutting instrument, and (ii) a second, high power operational mode for a second portion the cutting stroke cycle of the cutting instrument.

17 Claims, 23 Drawing Sheets

U.S. PATENT DOCUMENTS

| | | | |
|---|---|---|---|
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,529,235 A | 6/1996 | Boiarski et al. |
| 5,533,661 A | 7/1996 | Main et al. |
| 5,535,934 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,564,615 A | 10/1996 | Bishop et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,688,270 A | 11/1997 | Yates et al. |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,709,680 A | 1/1998 | Yates et al. |
| 5,711,472 A | 1/1998 | Bryan |
| 5,715,987 A | 2/1998 | Kelley et al. |
| 5,732,871 A | 3/1998 | Clark et al. |
| 5,732,872 A | 3/1998 | Bolduc et al. |
| 5,743,456 A | 4/1998 | Jones et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson, IV et al. |
| 5,901,895 A | 5/1999 | Heaton et al. |
| 5,937,951 A | 8/1999 | Izuchukwu et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,119,913 A | 9/2000 | Adams et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,302,311 B1 | 10/2001 | Adams et al. |
| 6,330,965 B1 | 12/2001 | Milliman et al. |
| 6,488,196 B1 | 12/2002 | Fenton, Jr. |
| 6,578,751 B2 | 6/2003 | Hartwick |
| 6,588,643 B2 | 7/2003 | Bolduc et al. |
| 6,619,529 B2 | 9/2003 | Green et al. |
| 6,644,532 B2 | 11/2003 | Green et al. |
| 6,681,978 B2 | 1/2004 | Geiste et al. |
| 6,716,233 B1 | 4/2004 | Whitman |
| 6,755,338 B2 | 6/2004 | Hahnen et al. |
| 6,769,594 B2 | 8/2004 | Orban, III |
| 6,786,382 B1 | 9/2004 | Hoffman |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,309 B2 | 1/2005 | Whitman et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,111,769 B2 | 9/2006 | Wales et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,147,138 B2 | 12/2006 | Shelton, IV |
| 7,168,604 B2 | 1/2007 | Milliman et al. |
| 7,182,239 B1 | 2/2007 | Myers |
| 7,225,964 B2 | 6/2007 | Mastri et al. |
| 7,237,708 B1 | 7/2007 | Guy et al. |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 * | 8/2008 | Shelton et al. ............. 227/175.1 |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |

| | | | | | | |
|---|---|---|---|---|---|---|
| 7,434,717 | B2 | 10/2008 | Shelton, IV et al. | 2005/0263563 A1 | 12/2005 | Racenet et al. |
| 7,438,209 | B1 | 10/2008 | Hess et al. | 2005/0274768 A1 | 12/2005 | Cummins et al. |
| 7,441,684 | B2 | 10/2008 | Shelton, IV et al. | 2006/0025811 A1 | 2/2006 | Shelton, IV |
| 7,441,685 | B1 | 10/2008 | Boudreaux | 2006/0025812 A1 | 2/2006 | Shelton, IV |
| 7,448,525 | B2 | 11/2008 | Shelton, IV et al. | 2006/0049229 A1 | 3/2006 | Milliman et al. |
| 7,455,208 | B2 | 11/2008 | Wales et al. | 2006/0180634 A1 | 8/2006 | Shelton, IV et al. |
| 7,481,347 | B2 | 1/2009 | Roy | 2006/0226196 A1 | 10/2006 | Hueil et al. |
| 7,481,349 | B2 | 1/2009 | Holsten et al. | 2006/0278680 A1 | 12/2006 | Viola et al. |
| 7,506,790 | B2 | 3/2009 | Shelton, IV | 2006/0278681 A1 | 12/2006 | Viola et al. |
| 7,510,107 | B2 | 3/2009 | Timm et al. | 2007/0023476 A1 | 2/2007 | Whitman et al. |
| 7,549,564 | B2 | 6/2009 | Boudreaux | 2007/0023477 A1 | 2/2007 | Whitman et al. |
| 7,559,450 | B2 | 7/2009 | Wales et al. | 2007/0045379 A1 | 3/2007 | Shelton, IV |
| 7,568,604 | B2 | 8/2009 | Ehrenfels et al. | 2007/0073340 A1 | 3/2007 | Shelton, IV et al. |
| 7,575,144 | B2 | 8/2009 | Ortiz et al. | 2007/0083234 A1 | 4/2007 | Shelton, IV et al. |
| 7,588,175 | B2 | 9/2009 | Timm et al. | 2007/0084897 A1 | 4/2007 | Shelton, IV et al. |
| 7,588,176 | B2 | 9/2009 | Timm et al. | 2007/0102452 A1 | 5/2007 | Shelton, IV et al. |
| 7,597,229 | B2 | 10/2009 | Boudreaux et al. | 2007/0102453 A1 | 5/2007 | Morgan et al. |
| 7,604,150 | B2 | 10/2009 | Boudreaux | 2007/0102472 A1 | 5/2007 | Shelton, IV |
| 7,604,151 | B2 | 10/2009 | Hess et al. | 2007/0102473 A1 | 5/2007 | Shelton, IV et al. |
| 7,624,902 | B2 | 12/2009 | Marczyk et al. | 2007/0102474 A1 | 5/2007 | Shelton, IV et al. |
| 7,631,793 | B2 | 12/2009 | Rethy et al. | 2007/0106317 A1 | 5/2007 | Shelton, IV et al. |
| 7,658,311 | B2 | 2/2010 | Boudreaux | 2007/0114261 A1 | 5/2007 | Ortiz et al. |
| 7,665,646 | B2 | 2/2010 | Prommersberger | 2007/0158385 A1 | 7/2007 | Hueil et al. |
| 7,669,747 | B2 | 3/2010 | Weisenburgh, II et al. | 2007/0170225 A1 | 7/2007 | Shelton, IV et al. |
| 7,673,782 | B2 | 3/2010 | Hess et al. | 2007/0175949 A1 | 8/2007 | Shelton, IV et al. |
| 7,699,204 | B2 | 4/2010 | Viola | 2007/0175950 A1 | 8/2007 | Shelton, IV et al. |
| 7,717,312 | B2 | 5/2010 | Beetel | 2007/0175951 A1 | 8/2007 | Shelton, IV et al. |
| 7,721,930 | B2 | 5/2010 | McKenna et al. | 2007/0175953 A1 | 8/2007 | Shelton, IV et al. |
| 7,726,537 | B2 | 6/2010 | Olson et al. | 2007/0175955 A1 * | 8/2007 | Shelton et al. ............. 227/178.1 |
| 7,726,538 | B2 | 6/2010 | Holsten et al. | 2007/0175956 A1 | 8/2007 | Swayze et al. |
| 7,731,072 | B2 | 6/2010 | Timm et al. | 2007/0175957 A1 | 8/2007 | Shelton, IV et al. |
| 7,735,703 | B2 | 6/2010 | Morgan et al. | 2007/0175958 A1 | 8/2007 | Shelton, IV et al. |
| 7,743,960 | B2 * | 6/2010 | Whitman et al. .......... 227/180.1 | 2007/0175959 A1 | 8/2007 | Shelton, IV et al. |
| 7,753,245 | B2 | 7/2010 | Boudreaux et al. | 2007/0175960 A1 | 8/2007 | Shelton, IV et al. |
| 7,766,209 | B2 | 8/2010 | Baxter, III et al. | 2007/0175961 A1 | 8/2007 | Shelton, IV et al. |
| 7,780,054 | B2 | 8/2010 | Wales | 2007/0175964 A1 * | 8/2007 | Shelton et al. ............. 227/180.1 |
| 7,784,662 | B2 | 8/2010 | Wales et al. | 2007/0179476 A1 | 8/2007 | Shelton, IV et al. |
| 7,793,812 | B2 | 9/2010 | Moore et al. | 2007/0194079 A1 | 8/2007 | Hueil et al. |
| 7,798,386 | B2 | 9/2010 | Schall et al. | 2007/0194080 A1 | 8/2007 | Swayze et al. |
| 7,810,692 | B2 | 10/2010 | Hall et al. | 2007/0194081 A1 | 8/2007 | Hueil et al. |
| 7,810,693 | B2 | 10/2010 | Broehl et al. | 2007/0194082 A1 | 8/2007 | Morgan et al. |
| 7,819,296 | B2 | 10/2010 | Hueil et al. | 2007/0221700 A1 | 9/2007 | Ortiz et al. |
| 7,819,297 | B2 | 10/2010 | Doll et al. | 2007/0221701 A1 | 9/2007 | Ortiz et al. |
| 7,819,298 | B2 | 10/2010 | Hall et al. | 2007/0225562 A1 | 9/2007 | Spivey et al. |
| 7,819,299 | B2 | 10/2010 | Shelton, IV et al. | 2007/0233053 A1 | 10/2007 | Shelton, IV et al. |
| 7,832,408 | B2 | 11/2010 | Shelton, IV et al. | 2007/0246505 A1 | 10/2007 | Pace-Floridia et al. |
| 7,832,611 | B2 | 11/2010 | Boyden et al. | 2007/0262116 A1 | 11/2007 | Hueil et al. |
| 7,832,612 | B2 | 11/2010 | Baxter, III et al. | 2007/0295780 A1 | 12/2007 | Shelton et al. |
| 7,837,080 | B2 | 11/2010 | Schwemberger | 2008/0029570 A1 | 2/2008 | Shelton et al. |
| 7,845,533 | B2 | 12/2010 | Marczyk et al. | 2008/0029573 A1 | 2/2008 | Shelton et al. |
| 7,845,537 | B2 * | 12/2010 | Shelton et al. ............. 227/180.1 | 2008/0029574 A1 | 2/2008 | Shelton et al. |
| 7,857,185 | B2 | 12/2010 | Swayze et al. | 2008/0029575 A1 | 2/2008 | Shelton et al. |
| 7,857,186 | B2 | 12/2010 | Baxter, III et al. | 2008/0029576 A1 | 2/2008 | Shelton et al. |
| 7,861,906 | B2 | 1/2011 | Doll et al. | 2008/0035701 A1 | 2/2008 | Racenet et al. |
| 7,866,527 | B2 | 1/2011 | Hall et al. | 2008/0041917 A1 | 2/2008 | Racenet et al. |
| 7,905,380 | B2 | 3/2011 | Shelton, IV et al. | 2008/0078800 A1 | 4/2008 | Hess et al. |
| 7,905,381 | B2 | 3/2011 | Baxter, III et al. | 2008/0078801 A1 | 4/2008 | Shelton et al. |
| 7,909,221 | B2 | 3/2011 | Viola et al. | 2008/0078802 A1 | 4/2008 | Hess et al. |
| 7,913,891 | B2 | 3/2011 | Doll et al. | 2008/0078803 A1 | 4/2008 | Shelton et al. |
| 7,918,377 | B2 | 4/2011 | Measamer et al. | 2008/0078804 A1 | 4/2008 | Shelton et al. |
| 7,922,061 | B2 | 4/2011 | Shelton, IV et al. | 2008/0078805 A1 | 4/2008 | Omaits et al. |
| 7,922,063 | B2 | 4/2011 | Zemlok et al. | 2008/0078806 A1 | 4/2008 | Omaits et al. |
| 7,950,560 | B2 | 5/2011 | Zemlok et al. | 2008/0078807 A1 | 4/2008 | Hess et al. |
| 7,954,684 | B2 | 6/2011 | Boudreaux | 2008/0078808 A1 | 4/2008 | Hess et al. |
| 7,954,686 | B2 | 6/2011 | Baxter, III et al. | 2008/0082115 A1 | 4/2008 | Morgan et al. |
| 7,959,051 | B2 | 6/2011 | Smith et al. | 2008/0082124 A1 | 4/2008 | Hess et al. |
| 7,980,443 | B2 | 7/2011 | Scheib et al. | 2008/0082125 A1 | 4/2008 | Murray et al. |
| 8,020,743 | B2 | 9/2011 | Shelton, IV | 2008/0082126 A1 | 4/2008 | Murray et al. |
| D650,074 | S | 12/2011 | Hunt et al. | 2008/0164296 A1 | 7/2008 | Shelton et al. |
| 2002/0117534 | A1 | 8/2002 | Green et al. | 2008/0167522 A1 | 7/2008 | Giordano et al. |
| 2003/0073981 | A1 * | 4/2003 | Whitman et al. .................. 606/1 | 2008/0167644 A1 | 7/2008 | Shelton et al. |
| 2004/0094597 | A1 * | 5/2004 | Whitman et al. .......... 227/180.1 | 2008/0167670 A1 | 7/2008 | Shelton et al. |
| 2004/0108357 | A1 | 6/2004 | Milliman et al. | 2008/0167671 A1 | 7/2008 | Giordano et al. |
| 2004/0164123 | A1 | 8/2004 | Racenet et al. | 2008/0167672 A1 | 7/2008 | Giordano et al. |
| 2004/0173659 | A1 | 9/2004 | Green et al. | 2008/0167736 A1 | 7/2008 | Swayze et al. |
| 2004/0232201 | A1 | 11/2004 | Wenchell et al. | 2008/0169328 A1 | 7/2008 | Shelton |
| 2005/0103819 | A1 | 5/2005 | Racenet et al. | 2008/0169329 A1 | 7/2008 | Shelton et al. |
| 2005/0184121 | A1 | 8/2005 | Heinrich | 2008/0169330 A1 | 7/2008 | Shelton et al. |
| 2005/0189397 | A1 | 9/2005 | Jankowski | 2008/0169331 A1 | 7/2008 | Shelton et al. |

| | | | | | | |
|---|---|---|---|---|---|---|
| 2008/0169332 A1 | 7/2008 | Shelton et al. | | 2010/0305552 A1 | 12/2010 | Shelton, IV et al. |
| 2008/0169333 A1 | 7/2008 | Shelton et al. | | 2010/0308100 A1 | 12/2010 | Boudreaux |
| 2008/0197167 A1 | 8/2008 | Viola et al. | | 2011/0006099 A1 | 1/2011 | Hall et al. |
| 2008/0210738 A1 | 9/2008 | Shelton et al. | | 2011/0006101 A1 | 1/2011 | Hall et al. |
| 2008/0237296 A1 | 10/2008 | Boudreaux et al. | | 2011/0006103 A1 | 1/2011 | Laurent et al. |
| 2008/0237298 A1 | 10/2008 | Schall et al. | | 2011/0011914 A1 | 1/2011 | Baxter, III et al. |
| 2008/0251568 A1 | 10/2008 | Zemlok et al. | | 2011/0011915 A1 | 1/2011 | Shelton, IV |
| 2008/0283570 A1 | 11/2008 | Boyden et al. | | 2011/0017801 A1 | 1/2011 | Zemlok et al. |
| 2008/0290134 A1 | 11/2008 | Bettuchi et al. | | 2011/0022032 A1* | 1/2011 | Zemlok et al. ............ 606/1 |
| 2008/0296346 A1 | 12/2008 | Shelton, IV et al. | | 2011/0024477 A1 | 2/2011 | Hall et al. |
| 2008/0300580 A1 | 12/2008 | Shelton, IV et al. | | 2011/0024478 A1 | 2/2011 | Shelton, IV |
| 2008/0308602 A1 | 12/2008 | Timm et al. | | 2011/0024479 A1 | 2/2011 | Swensgard et al. |
| 2008/0308603 A1 | 12/2008 | Shelton, IV et al. | | 2011/0036887 A1 | 2/2011 | Zemlok et al. |
| 2008/0308608 A1 | 12/2008 | Prommersberger | | 2011/0042441 A1 | 2/2011 | Shelton, IV et al. |
| 2008/0314960 A1 | 12/2008 | Marczyk et al. | | 2011/0060363 A1 | 3/2011 | Hess et al. |
| 2009/0001121 A1 | 1/2009 | Hess et al. | | 2011/0062212 A1 | 3/2011 | Shelton, IV et al. |
| 2009/0001122 A1 | 1/2009 | Prommersberger et al. | | 2011/0068145 A1 | 3/2011 | Bedi et al. |
| 2009/0001124 A1 | 1/2009 | Hess et al. | | 2011/0068148 A1 | 3/2011 | Hall et al. |
| 2009/0001130 A1 | 1/2009 | Hess et al. | | 2011/0084112 A1 | 4/2011 | Kostrzewski |
| 2009/0005807 A1 | 1/2009 | Hess et al. | | 2011/0084113 A1 | 4/2011 | Bedi et al. |
| 2009/0005808 A1 | 1/2009 | Hess et al. | | 2011/0084115 A1 | 4/2011 | Bedi et al. |
| 2009/0005809 A1 | 1/2009 | Hess et al. | | 2011/0087276 A1 | 4/2011 | Bedi et al. |
| 2009/0012556 A1 | 1/2009 | Boudreaux et al. | | 2011/0101065 A1 | 5/2011 | Milliman |
| 2009/0057369 A1 | 3/2009 | Smith et al. | | 2011/0114697 A1 | 5/2011 | Baxter, III et al. |
| 2009/0076534 A1 | 3/2009 | Shelton, IV et al. | | 2011/0114698 A1 | 5/2011 | Baxter, III et al. |
| 2009/0108048 A1 | 4/2009 | Zemlok et al. | | 2011/0114699 A1 | 5/2011 | Baxter, III et al. |
| 2009/0114701 A1 | 5/2009 | Zemlok et al. | | 2011/0114700 A1 | 5/2011 | Baxter, III et al. |
| 2009/0149871 A9 | 6/2009 | Kagan et al. | | 2011/0118761 A1 | 5/2011 | Baxter, III et al. |
| 2009/0206125 A1 | 8/2009 | Huitema et al. | | 2011/0121051 A1 | 5/2011 | Shelton, IV et al. |
| 2009/0206126 A1 | 8/2009 | Huitema et al. | | 2011/0121052 A1 | 5/2011 | Shelton, IV et al. |
| 2009/0206131 A1 | 8/2009 | Weisenburgh, II et al. | | 2011/0125176 A1 | 5/2011 | Yates et al. |
| 2009/0206132 A1 | 8/2009 | Hueil et al. | | 2011/0125177 A1 | 5/2011 | Yates et al. |
| 2009/0206133 A1 | 8/2009 | Morgan et al. | | 2011/0132962 A1 | 6/2011 | Hall et al. |
| 2009/0206137 A1 | 8/2009 | Hall et al. | | 2011/0132963 A1 | 6/2011 | Giordano et al. |
| 2009/0206139 A1 | 8/2009 | Hall et al. | | 2011/0132964 A1 | 6/2011 | Weisenburgh, II et al. |
| 2009/0206141 A1 | 8/2009 | Huitema et al. | | 2011/0132965 A1 | 6/2011 | Moore et al. |
| 2009/0206142 A1 | 8/2009 | Huitema et al. | | 2011/0139852 A1 | 6/2011 | Zingman |
| 2009/0206143 A1 | 8/2009 | Huitema et al. | | 2011/0144430 A1 | 6/2011 | Spivey et al. |
| 2009/0209946 A1 | 8/2009 | Swayze et al. | | 2011/0147433 A1 | 6/2011 | Shelton, IV et al. |
| 2009/0218384 A1 | 9/2009 | Aranyi | | 2011/0147434 A1 | 6/2011 | Hueil et al. |
| 2009/0242610 A1 | 10/2009 | Shelton, IV et al. | | 2011/0155780 A1 | 6/2011 | Boudreaux |
| 2009/0255974 A1 | 10/2009 | Viola | | 2011/0155781 A1 | 6/2011 | Swensgard et al. |
| 2009/0255975 A1 | 10/2009 | Zemlok et al. | | 2011/0155785 A1 | 6/2011 | Laurent et al. |
| 2009/0255976 A1 | 10/2009 | Marczyk et al. | | 2011/0155787 A1 | 6/2011 | Baxter, III et al. |
| 2009/0255977 A1 | 10/2009 | Zemlok | | 2011/0163147 A1 | 7/2011 | Laurent et al. |
| 2010/0001036 A1* | 1/2010 | Marczyk et al. ............ 227/175.1 | | 2011/0174860 A1 | 7/2011 | Shelton, IV et al. |
| 2010/0032470 A1 | 2/2010 | Hess et al. | | 2011/0174863 A1 | 7/2011 | Shelton, IV et al. |
| 2010/0065605 A1 | 3/2010 | Shelton, IV et al. | | 2011/0192882 A1 | 8/2011 | Hess et al. |
| 2010/0069942 A1 | 3/2010 | Shelton, IV | | 2011/0226837 A1 | 9/2011 | Baxter, III et al. |
| 2010/0072254 A1 | 3/2010 | Aranyi et al. | | 2011/0233258 A1 | 9/2011 | Boudreaux |
| 2010/0076475 A1 | 3/2010 | Yates et al. | | 2011/0253766 A1 | 10/2011 | Baxter, III et al. |
| 2010/0089970 A1 | 4/2010 | Smith et al. | | 2011/0288573 A1 | 11/2011 | Yates et al. |
| 2010/0089972 A1 | 4/2010 | Marczyk | | 2011/0290851 A1 | 12/2011 | Shelton, IV |
| 2010/0127042 A1 | 5/2010 | Shelton, IV | | 2011/0290853 A1 | 12/2011 | Shelton, IV et al. |
| 2010/0133317 A1 | 6/2010 | Shelton, IV et al. | | 2011/0290854 A1 | 12/2011 | Timm et al. |
| 2010/0133318 A1 | 6/2010 | Boudreaux | | 2011/0290855 A1 | 12/2011 | Moore et al. |
| 2010/0179382 A1 | 7/2010 | Shelton, IV et al. | | 2011/0290856 A1 | 12/2011 | Shelton, IV et al. |
| 2010/0181364 A1 | 7/2010 | Shelton, IV et al. | | 2011/0290857 A1 | 12/2011 | Shelton, IV et al. |
| 2010/0193566 A1 | 8/2010 | Scheib et al. | | 2011/0295242 A1 | 12/2011 | Spivey et al. |
| 2010/0193567 A1 | 8/2010 | Scheib et al. | | 2011/0295269 A1 | 12/2011 | Swensgard et al. |
| 2010/0193568 A1 | 8/2010 | Scheib et al. | | 2011/0295270 A1 | 12/2011 | Giordano et al. |
| 2010/0193569 A1 | 8/2010 | Yates et al. | | 2011/0295295 A1 | 12/2011 | Shelton, IV et al. |
| 2010/0198220 A1 | 8/2010 | Boudreaux et al. | | 2012/0024934 A1 | 2/2012 | Shelton, IV et al. |
| 2010/0200637 A1 | 8/2010 | Beetel | | 2012/0024935 A1 | 2/2012 | Shelton, IV et al. |
| 2010/0213241 A1 | 8/2010 | Bedi et al. | | 2012/0024936 A1 | 2/2012 | Baxter, III et al. |
| 2010/0222901 A1 | 9/2010 | Swayze et al. | | 2012/0029272 A1 | 2/2012 | Shelton, IV et al. |
| 2010/0224669 A1 | 9/2010 | Shelton, IV et al. | | 2012/0029544 A1 | 2/2012 | Shelton, IV et al. |
| 2010/0237132 A1 | 9/2010 | Measamer et al. | | 2012/0029547 A1 | 2/2012 | Shelton, IV et al. |
| 2010/0243707 A1 | 9/2010 | Olson et al. | | | | |
| 2010/0243708 A1 | 9/2010 | Aranyi et al. | | FOREIGN PATENT DOCUMENTS | | |
| 2010/0243709 A1 | 9/2010 | Hess et al. | | CA | 2512960 A1 | 1/2006 |
| 2010/0264193 A1 | 10/2010 | Huang et al. | | CA | 2514274 A1 | 1/2006 |
| 2010/0264194 A1 | 10/2010 | Huang et al. | | CN | 1868411 A | 11/2006 |
| 2010/0294827 A1 | 11/2010 | Boyden et al. | | CN | 1915180 A | 2/2007 |
| 2010/0294829 A1 | 11/2010 | Giordano et al. | | DE | 273689 C | 5/1914 |
| 2010/0301095 A1 | 12/2010 | Shelton, IV et al. | | DE | 1775926 A | 1/1972 |
| 2010/0301096 A1 | 12/2010 | Moore et al. | | DE | 3036217 A1 | 4/1982 |
| | | | | DE | 3210466 A1 | 9/1983 |
| | | | | DE | 9412228 U | 9/1994 |

| | | | | | | | |
|---|---|---|---|---|---|---|---|
| DE | 19509116 | A1 | 9/1996 | EP | 1050278 | A1 | 11/2000 |
| DE | 19851291 | A1 | 1/2000 | EP | 1053719 | A1 | 11/2000 |
| DE | 19924311 | A1 | 11/2000 | EP | 1053720 | A1 | 11/2000 |
| DE | 69328576 | T2 | 1/2001 | EP | 1055399 | A1 | 11/2000 |
| DE | 10052679 | A1 | 5/2001 | EP | 1055400 | A1 | 11/2000 |
| DE | 20112837 | U1 | 10/2001 | EP | 1080694 | A1 | 3/2001 |
| DE | 20121753 | U1 | 4/2003 | EP | 1090592 | A1 | 4/2001 |
| DE | 10314072 | A1 | 10/2004 | EP | 1095627 | A1 | 5/2001 |
| DE | 202007003114 | U1 | 6/2007 | EP | 1256318 | B1 | 5/2001 |
| EP | 0122046 | A1 | 10/1984 | EP | 0806914 | B1 | 9/2001 |
| EP | 0070230 | B1 | 10/1985 | EP | 0768840 | B1 | 12/2001 |
| EP | 0387980 | B1 | 10/1985 | EP | 0908152 | B1 | 1/2002 |
| EP | 0033548 | B1 | 5/1986 | EP | 0872213 | B1 | 5/2002 |
| EP | 0276104 | A2 | 7/1988 | EP | 0862386 | B1 | 6/2002 |
| EP | 0248844 | B1 | 1/1993 | EP | 0949886 | B1 | 9/2002 |
| EP | 0545029 | A1 | 6/1993 | EP | 1238634 | A2 | 9/2002 |
| EP | 0277959 | B1 | 10/1993 | EP | 0858295 | B1 | 12/2002 |
| EP | 0233940 | B1 | 11/1993 | EP | 0656188 | B1 | 1/2003 |
| EP | 0261230 | B1 | 11/1993 | EP | 1284120 | A1 | 2/2003 |
| EP | 0639349 | A2 | 2/1994 | EP | 1287788 | A1 | 3/2003 |
| EP | 0324636 | B1 | 3/1994 | EP | 0717966 | B1 | 4/2003 |
| EP | 0593920 | A1 | 4/1994 | EP | 0869742 | B1 | 5/2003 |
| EP | 0523174 | B1 | 6/1994 | EP | 0829235 | B1 | 6/2003 |
| EP | 0600182 | A2 | 6/1994 | EP | 0887046 | B1 | 7/2003 |
| EP | 0310431 | B1 | 11/1994 | EP | 0852480 | B1 | 8/2003 |
| EP | 0375302 | B1 | 11/1994 | EP | 0891154 | B1 | 9/2003 |
| EP | 0376562 | B1 | 11/1994 | EP | 0813843 | B1 | 10/2003 |
| EP | 0630612 | A1 | 12/1994 | EP | 0873089 | B1 | 10/2003 |
| EP | 0634144 | A1 | 1/1995 | EP | 0856326 | B1 | 11/2003 |
| EP | 0646356 | A2 | 4/1995 | EP | 1374788 | A1 | 1/2004 |
| EP | 0646357 | A1 | 4/1995 | EP | 0741996 | B1 | 2/2004 |
| EP | 0653189 | A2 | 5/1995 | EP | 0814712 | B1 | 2/2004 |
| EP | 0669104 | A1 | 8/1995 | EP | 1402837 | A1 | 3/2004 |
| EP | 0511470 | B1 | 10/1995 | EP | 0705570 | B1 | 4/2004 |
| EP | 0679367 | A2 | 11/1995 | EP | 0959784 | B1 | 4/2004 |
| EP | 0392547 | B1 | 12/1995 | EP | 1407719 | A2 | 4/2004 |
| EP | 0685204 | A1 | 12/1995 | EP | 1086713 | B1 | 5/2004 |
| EP | 0364216 | B1 | 1/1996 | EP | 0996378 | B1 | 6/2004 |
| EP | 0699418 | A1 | 3/1996 | EP | 1426012 | A1 | 6/2004 |
| EP | 0702937 | A1 | 3/1996 | EP | 0833593 | B2 | 7/2004 |
| EP | 0705571 | A1 | 4/1996 | EP | 1442694 | A1 | 8/2004 |
| EP | 0711611 | A2 | 5/1996 | EP | 0888749 | B1 | 9/2004 |
| EP | 0484677 | B2 | 6/1996 | EP | 0959786 | B1 | 9/2004 |
| EP | 0541987 | B1 | 7/1996 | EP | 1459695 | A1 | 9/2004 |
| EP | 0667119 | B1 | 7/1996 | EP | 1473819 | A1 | 11/2004 |
| EP | 0708618 | B1 | 3/1997 | EP | 1477119 | A1 | 11/2004 |
| EP | 0770355 | A1 | 5/1997 | EP | 1479345 | A1 | 11/2004 |
| EP | 0503662 | B1 | 6/1997 | EP | 1479347 | A1 | 11/2004 |
| EP | 0447121 | B1 | 7/1997 | EP | 1479348 | A1 | 11/2004 |
| EP | 0625077 | B1 | 7/1997 | EP | 0754437 | B2 | 12/2004 |
| EP | 0633749 | B1 | 8/1997 | EP | 1025807 | B1 | 12/2004 |
| EP | 0710090 | B1 | 8/1997 | EP | 1001710 | B1 | 1/2005 |
| EP | 0578425 | B1 | 9/1997 | EP | 1520521 | A1 | 4/2005 |
| EP | 0625335 | B1 | 11/1997 | EP | 1520523 | A1 | 4/2005 |
| EP | 0552423 | B1 | 1/1998 | EP | 1520525 | A1 | 4/2005 |
| EP | 0592244 | B1 | 1/1998 | EP | 1522264 | A1 | 4/2005 |
| EP | 0648476 | B1 | 1/1998 | EP | 1523942 | A2 | 4/2005 |
| EP | 0649290 | B1 | 3/1998 | EP | 1550408 | A1 | 7/2005 |
| EP | 0598618 | B1 | 9/1998 | EP | 1557129 | A1 | 7/2005 |
| EP | 0676173 | B1 | 9/1998 | EP | 1064883 | B1 | 8/2005 |
| EP | 0678007 | B1 | 9/1998 | EP | 1067876 | B1 | 8/2005 |
| EP | 0603472 | B1 | 11/1998 | EP | 0870473 | B1 | 9/2005 |
| EP | 0605351 | B1 | 11/1998 | EP | 1157666 | B1 | 9/2005 |
| EP | 0878169 | A1 | 11/1998 | EP | 0880338 | B1 | 10/2005 |
| EP | 0879742 | A1 | 11/1998 | EP | 1158917 | B1 | 11/2005 |
| EP | 0695144 | B1 | 12/1998 | EP | 1344498 | B1 | 11/2005 |
| EP | 0722296 | B1 | 12/1998 | EP | 1330989 | B1 | 12/2005 |
| EP | 0760230 | B1 | 2/1999 | EP | 0771176 | B2 | 1/2006 |
| EP | 0623316 | B1 | 3/1999 | EP | 1621138 | A2 | 2/2006 |
| EP | 0650701 | B1 | 3/1999 | EP | 1621139 | A2 | 2/2006 |
| EP | 0537572 | B1 | 6/1999 | EP | 1621141 | A2 | 2/2006 |
| EP | 0923907 | A1 | 6/1999 | EP | 1621145 | A2 | 2/2006 |
| EP | 0843906 | B1 | 3/2000 | EP | 1621151 | A2 | 2/2006 |
| EP | 0552050 | B1 | 5/2000 | EP | 1034746 | B1 | 3/2006 |
| EP | 0833592 | B1 | 5/2000 | EP | 1632191 | A2 | 3/2006 |
| EP | 0830094 | B1 | 9/2000 | EP | 1065981 | B1 | 5/2006 |
| EP | 1034747 | A1 | 9/2000 | EP | 1082944 | B1 | 5/2006 |
| EP | 1034748 | A1 | 9/2000 | EP | 1652481 | A2 | 5/2006 |
| EP | 0694290 | B1 | 11/2000 | | | | |

| | | | | | | |
|---|---|---|---|---|---|---|
| EP | 1382303 B1 | 6/2006 | | JP | 8033641 A | 2/1996 |
| EP | 1253866 B1 | 7/2006 | | JP | 8229050 A | 9/1996 |
| EP | 1032318 B1 | 8/2006 | | JP | 2000033071 A | 2/2000 |
| EP | 1045672 B1 | 8/2006 | | JP | 2000171730 A | 6/2000 |
| EP | 1617768 B1 | 8/2006 | | JP | 2000287987 A | 10/2000 |
| EP | 1693015 A2 | 8/2006 | | JP | 2000325303 A | 11/2000 |
| EP | 1400214 B1 | 9/2006 | | JP | 2001286477 A | 10/2001 |
| EP | 1702567 A2 | 9/2006 | | JP | 2002143078 A | 5/2002 |
| EP | 1129665 B1 | 11/2006 | | JP | 2002369820 A | 12/2002 |
| EP | 1400206 B1 | 11/2006 | | JP | 2005505322 T | 2/2005 |
| EP | 1721568 A1 | 11/2006 | | JP | 2005103293 A | 4/2005 |
| EP | 1256317 B1 | 12/2006 | | JP | 2005131163 A | 5/2005 |
| EP | 1728473 A1 | 12/2006 | | JP | 2005131164 A | 5/2005 |
| EP | 1728475 A2 | 12/2006 | | JP | 2005131173 A | 5/2005 |
| EP | 1479346 B1 | 1/2007 | | JP | 2005131211 A | 5/2005 |
| EP | 1484024 B1 | 1/2007 | | JP | 2005131212 A | 5/2005 |
| EP | 1754445 A2 | 2/2007 | | JP | 2005137423 A | 6/2005 |
| EP | 1759812 A1 | 3/2007 | | JP | 2005152416 A | 6/2005 |
| EP | 1767163 A1 | 3/2007 | | JP | 2006-281405 A | 10/2006 |
| EP | 1769756 A1 | 4/2007 | | RU | 2008830 C1 | 3/1994 |
| EP | 1769758 A1 | 4/2007 | | RU | 2187249 C2 | 8/2002 |
| EP | 1581128 B1 | 5/2007 | | RU | 2225170 C2 | 3/2004 |
| EP | 1785097 A2 | 5/2007 | | SU | 189517 A | 1/1967 |
| EP | 1790293 A2 | 5/2007 | | SU | 328636 A | 9/1972 |
| EP | 1800610 A1 | 6/2007 | | SU | 886900 A | 12/1981 |
| EP | 1300117 B1 | 8/2007 | | SU | 1009439 A | 4/1983 |
| EP | 1813199 A1 | 8/2007 | | SU | 1333319 A2 | 8/1987 |
| EP | 1813201 A1 | 8/2007 | | SU | 1377053 A1 | 2/1988 |
| EP | 1813203 A2 | 8/2007 | | SU | 1561964 A1 | 5/1990 |
| EP | 1813207 A1 | 8/2007 | | SU | 1722476 A1 | 3/1992 |
| EP | 1813209 A1 | 8/2007 | | WO | WO 91/15157 A1 | 10/1991 |
| EP | 1487359 B1 | 10/2007 | | WO | WO 92/20295 A1 | 11/1992 |
| EP | 1599146 B1 | 10/2007 | | WO | WO 92/21300 A1 | 12/1992 |
| EP | 1839596 A1 | 10/2007 | | WO | WO 93/08755 A1 | 5/1993 |
| EP | 1402821 B1 | 12/2007 | | WO | WO 93/13718 A1 | 7/1993 |
| EP | 1872727 A1 | 1/2008 | | WO | WO 93/14690 A1 | 8/1993 |
| EP | 1897502 A1 | 3/2008 | | WO | WO 93/15648 A1 | 8/1993 |
| EP | 1330201 B1 | 6/2008 | | WO | WO 93/15850 A1 | 8/1993 |
| EP | 1702568 B1 | 7/2008 | | WO | WO 93/19681 A1 | 10/1993 |
| EP | 1943957 A2 | 7/2008 | | WO | WO 94/00060 A1 | 1/1994 |
| EP | 1943976 A2 | 7/2008 | | WO | WO 94/11057 A1 | 5/1994 |
| EP | 1593337 B1 | 8/2008 | | WO | WO 94/12108 A1 | 6/1994 |
| EP | 1970014 A1 | 9/2008 | | WO | WO 94/18893 A1 | 9/1994 |
| EP | 1980213 A2 | 10/2008 | | WO | WO 94/22378 A1 | 10/1994 |
| EP | 1759645 B1 | 11/2008 | | WO | WO 94/23659 A1 | 10/1994 |
| EP | 1990014 A2 | 11/2008 | | WO | WO 95/02369 A1 | 1/1995 |
| EP | 1693008 B1 | 12/2008 | | WO | WO 95/03743 A1 | 2/1995 |
| EP | 1759640 B1 | 12/2008 | | WO | WO 95/06817 A1 | 3/1995 |
| EP | 2000102 A2 | 12/2008 | | WO | WO 95/09576 A1 | 4/1995 |
| EP | 1736104 B1 | 3/2009 | | WO | WO 95/09577 A1 | 4/1995 |
| EP | 1749486 B1 | 3/2009 | | WO | WO 95/14436 A1 | 6/1995 |
| EP | 1721576 B1 | 4/2009 | | WO | WO 95/17855 A1 | 7/1995 |
| EP | 1733686 B1 | 4/2009 | | WO | WO 95/18383 A1 | 7/1995 |
| EP | 2044890 A1 | 4/2009 | | WO | WO 95/18572 A1 | 7/1995 |
| EP | 1745748 B1 | 8/2009 | | WO | WO 95/19739 A1 | 7/1995 |
| EP | 2090256 A2 | 8/2009 | | WO | WO 95/20360 A1 | 8/1995 |
| EP | 1813208 B1 | 11/2009 | | WO | WO 95/23557 A1 | 9/1995 |
| EP | 1607050 B1 | 12/2009 | | WO | WO 95/24865 A1 | 9/1995 |
| EP | 1566150 B1 | 4/2010 | | WO | WO 95/25471 A3 | 9/1995 |
| EP | 1813206 B1 | 4/2010 | | WO | WO 95/26562 A1 | 10/1995 |
| EP | 1769754 B1 | 6/2010 | | WO | WO 95/29639 A1 | 11/1995 |
| EP | 1535565 B1 | 10/2010 | | WO | WO 96/04858 A1 | 2/1996 |
| EP | 1702570 B1 | 10/2010 | | WO | WO 96/19151 A1 | 6/1996 |
| EP | 1785098 B1 | 10/2010 | | WO | WO 96/19152 A1 | 6/1996 |
| EP | 1813205 B1 | 6/2011 | | WO | WO 96/20652 A1 | 7/1996 |
| FR | 999646 A | 2/1952 | | WO | WO 96/21119 A1 | 7/1996 |
| FR | 1112936 A | 3/1956 | | WO | WO 96/22055 A1 | 7/1996 |
| FR | 2765794 A | 1/1999 | | WO | WO 96/23448 A1 | 8/1996 |
| GB | 939929 A | 10/1963 | | WO | WO 96/24301 A1 | 8/1996 |
| GB | 1210522 A | 10/1970 | | WO | WO 96/27337 A1 | 9/1996 |
| GB | 1217159 A | 12/1970 | | WO | WO 96/31155 A1 | 10/1996 |
| GB | 1339394 A | 12/1973 | | WO | WO 96/35464 A1 | 11/1996 |
| GB | 2109241 A | 6/1983 | | WO | WO 96/39085 A1 | 12/1996 |
| GB | 2272159 A | 5/1994 | | WO | WO 96/39086 A1 | 12/1996 |
| GB | 2284242 A | 5/1995 | | WO | WO 96/39087 A1 | 12/1996 |
| GB | 2336214 A | 10/1999 | | WO | WO 96/39088 A1 | 12/1996 |
| GB | 2425903 A | 11/2006 | | WO | WO 96/39089 A1 | 12/1996 |
| JP | 6007357 A | 1/1994 | | WO | WO 97/00646 A1 | 1/1997 |
| JP | 7051273 A | 2/1995 | | WO | WO 97/00647 A1 | 1/1997 |

| | | | | | | |
|---|---|---|---|---|---|---|
| WO | WO 97/06582 | A1 | 2/1997 | WO | WO 03/055402 A1 | 7/2003 |
| WO | WO 97/10763 | A1 | 3/1997 | WO | WO 03/057048 A1 | 7/2003 |
| WO | WO 97/10764 | A1 | 3/1997 | WO | WO 03/057058 A1 | 7/2003 |
| WO | WO 97/11648 | A2 | 4/1997 | WO | WO 03/063694 A1 | 8/2003 |
| WO | WO 97/11649 | A1 | 4/1997 | WO | WO 03/077769 A1 | 9/2003 |
| WO | WO 97/15237 | A1 | 5/1997 | WO | WO 03/079911 A1 | 10/2003 |
| WO | WO 97/24073 | A1 | 7/1997 | WO | WO 03/082126 A1 | 10/2003 |
| WO | WO 97/24993 | A1 | 7/1997 | WO | WO 03/088845 A2 | 10/2003 |
| WO | WO 97/30644 | A1 | 8/1997 | WO | WO 03/090630 A2 | 11/2003 |
| WO | WO 97/34533 | A1 | 9/1997 | WO | WO 03/094743 A1 | 11/2003 |
| WO | WO 97/37598 | A1 | 10/1997 | WO | WO 03/094745 A1 | 11/2003 |
| WO | WO 97/39688 | A2 | 10/1997 | WO | WO 03/094746 A1 | 11/2003 |
| WO | WO 98/17180 | A1 | 4/1998 | WO | WO 03/094747 A1 | 11/2003 |
| WO | WO 98/27880 | A1 | 7/1998 | WO | WO 03/101313 A1 | 12/2003 |
| WO | WO 98/30153 | A1 | 7/1998 | WO | WO 03/105698 A2 | 12/2003 |
| WO | WO 98/47436 | A1 | 10/1998 | WO | WO 03/105702 A2 | 12/2003 |
| WO | WO 99/03407 | A1 | 1/1999 | WO | WO 2004/006980 A2 | 1/2004 |
| WO | WO 99/03408 | A1 | 1/1999 | WO | WO 2004/019769 A1 | 3/2004 |
| WO | WO 99/03409 | A1 | 1/1999 | WO | WO 2004/021868 A2 | 3/2004 |
| WO | WO 99/12483 | A1 | 3/1999 | WO | WO 2004/028585 A2 | 4/2004 |
| WO | WO 99/12487 | A1 | 3/1999 | WO | WO 2004/032754 A2 | 4/2004 |
| WO | WO 99/12488 | A1 | 3/1999 | WO | WO 2004/032760 A2 | 4/2004 |
| WO | WO 99/15086 | A1 | 4/1999 | WO | WO 2004/032762 A1 | 4/2004 |
| WO | WO 99/15091 | A1 | 4/1999 | WO | WO 2004/032763 A2 | 4/2004 |
| WO | WO 99/23933 | A2 | 5/1999 | WO | WO 2004/034875 A2 | 4/2004 |
| WO | WO 99/23959 | A1 | 5/1999 | WO | WO 2004/047626 A1 | 6/2004 |
| WO | WO 99/25261 | A1 | 5/1999 | WO | WO 2004/047653 A2 | 6/2004 |
| WO | WO 99/29244 | A1 | 6/1999 | WO | WO 2004/049956 A2 | 6/2004 |
| WO | WO 99/34744 | A1 | 7/1999 | WO | WO 2004/052426 A2 | 6/2004 |
| WO | WO 99/45849 | A1 | 9/1999 | WO | WO 2004/056276 A1 | 7/2004 |
| WO | WO 99/48430 | A1 | 9/1999 | WO | WO 2004/056277 A1 | 7/2004 |
| WO | WO 99/51158 | A1 | 10/1999 | WO | WO 2004/062516 A1 | 7/2004 |
| WO | WO 00/24322 | A1 | 5/2000 | WO | WO 2004/078050 A2 | 9/2004 |
| WO | WO 00/24330 | A1 | 5/2000 | WO | WO 2004/078051 A2 | 9/2004 |
| WO | WO 00/41638 | A1 | 7/2000 | WO | WO 2004/086987 A1 | 10/2004 |
| WO | WO 00/48506 | A1 | 8/2000 | WO | WO 2004/096015 A2 | 11/2004 |
| WO | WO 00/53112 | A2 | 9/2000 | WO | WO 2004/096057 A2 | 11/2004 |
| WO | WO 00/54653 | A1 | 9/2000 | WO | WO 2004/103157 A2 | 12/2004 |
| WO | WO 00/57796 | A1 | 10/2000 | WO | WO 2004/105593 A1 | 12/2004 |
| WO | WO 00/64365 | A1 | 11/2000 | WO | WO 2004/105621 A1 | 12/2004 |
| WO | WO 00/72762 | A1 | 12/2000 | WO | WO 2004/112618 A2 | 12/2004 |
| WO | WO 00/72765 | A1 | 12/2000 | WO | WO 2004/112652 A2 | 12/2004 |
| WO | WO 01/03587 | A1 | 1/2001 | WO | WO 2005/027983 A2 | 3/2005 |
| WO | WO 01/05702 | A1 | 1/2001 | WO | WO 2005/037329 A2 | 4/2005 |
| WO | WO 01/10482 | A1 | 2/2001 | WO | WO 2005/044078 A2 | 5/2005 |
| WO | WO 01/35845 | A1 | 5/2001 | WO | WO 2005/055846 A1 | 6/2005 |
| WO | WO 01/54594 | A1 | 8/2001 | WO | WO 2005/072634 A2 | 8/2005 |
| WO | WO 01/58371 | A1 | 8/2001 | WO | WO 2005/078892 A1 | 8/2005 |
| WO | WO 01/62158 | A2 | 8/2001 | WO | WO 2005/096954 A2 | 10/2005 |
| WO | WO 01/62161 | A1 | 8/2001 | WO | WO 2005/112806 A2 | 12/2005 |
| WO | WO 01/62162 | A1 | 8/2001 | WO | WO 2005/112808 A1 | 12/2005 |
| WO | WO 01/62164 | A2 | 8/2001 | WO | WO 2005/115251 A2 | 12/2005 |
| WO | WO 01/62169 | A2 | 8/2001 | WO | WO 2005/117735 A1 | 12/2005 |
| WO | WO 01/78605 | A2 | 10/2001 | WO | WO 2005/122936 A1 | 12/2005 |
| WO | WO 01/91646 | A1 | 12/2001 | WO | WO 2006/027014 A1 | 3/2006 |
| WO | WO 02/07608 | A2 | 1/2002 | WO | WO 2006/044490 A2 | 4/2006 |
| WO | WO 02/07618 | A1 | 1/2002 | WO | WO 2006/044581 A2 | 4/2006 |
| WO | WO 02/17799 | A1 | 3/2002 | WO | WO 2006/044810 A2 | 4/2006 |
| WO | WO 02/19920 | A1 | 3/2002 | WO | WO 2006/051252 A1 | 5/2006 |
| WO | WO 02/19932 | A1 | 3/2002 | WO | WO 2006/059067 A1 | 6/2006 |
| WO | WO 02/30297 | A2 | 4/2002 | WO | WO 2006/083748 A1 | 8/2006 |
| WO | WO 02/32322 | A2 | 4/2002 | WO | WO 2006/092563 A1 | 9/2006 |
| WO | WO 02/36028 | A1 | 5/2002 | WO | WO 2006/092565 A1 | 9/2006 |
| WO | WO 02/43571 | A2 | 6/2002 | WO | WO 2006/115958 A1 | 11/2006 |
| WO | WO 02/058568 | A1 | 8/2002 | WO | WO 2006/125940 A1 | 11/2006 |
| WO | WO 02/060328 | A1 | 8/2002 | WO | WO 2006/132992 A1 | 12/2006 |
| WO | WO 02/067785 | A2 | 9/2002 | WO | WO 2007/002180 A2 | 1/2007 |
| WO | WO 02/098302 | A1 | 12/2002 | WO | WO 2007/016290 A2 | 2/2007 |
| WO | WO 03/000138 | A2 | 1/2003 | WO | WO 2007/018898 A2 | 2/2007 |
| WO | WO 03/001329 | A2 | 1/2003 | WO | WO 2007/098220 A2 | 8/2007 |
| WO | WO 03/013363 | A1 | 2/2003 | WO | WO 2007/121579 A1 | 11/2007 |
| WO | WO 03/015604 | A2 | 2/2003 | WO | WO 2007/137304 A2 | 11/2007 |
| WO | WO 03/020106 | A2 | 3/2003 | WO | WO 2007/139734 A2 | 12/2007 |
| WO | WO 03/020139 | A2 | 3/2003 | WO | WO 2007/142625 A2 | 12/2007 |
| WO | WO 03/024339 | A1 | 3/2003 | WO | WO 2008/021969 A2 | 2/2008 |
| WO | WO 03/079909 | A3 | 3/2003 | WO | WO 2008/039270 A1 | 4/2008 |
| WO | WO 03/030743 | A2 | 4/2003 | WO | WO 2008/045383 A2 | 4/2008 |
| WO | WO 03/037193 | A1 | 5/2003 | WO | WO 2008/109125 A1 | 9/2008 |
| WO | WO 03/047436 | A3 | 6/2003 | WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

European Search Report for 09252253.1, Mar. 21, 2011 (5 pages).

U.S. Appl. No. 12/031,556, filed Feb. 14, 2008.
U.S. Appl. No. 12/031,567, filed Feb. 14, 2008.
U.S. Appl. No. 12/031,573, filed Feb. 14, 2008.
U.S. Appl. No. 12/032,024, filed Feb. 15, 2008.

\* cited by examiner

MOTOR-DRIVEN SURGICAL CUTTING
INSTRUMENT

BACKGROUND

Surgical staplers are used to simultaneously make a longitudinal incision in tissue and apply lines of staples on opposing sides of the incision. Such instruments commonly include an end effector having a pair of cooperating jaw members that, if the instrument is intended for endoscopic or laparoscopic applications, are capable of passing through a cannula passageway. One of the jaw members receives a staple cartridge having at least two laterally spaced rows of staples—one on each side of the knife channel. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil. Simultaneously, a cutting instrument (or knife) is drawn distally along the jaw member so that the clamped tissue is cut and fastened (e.g., stapled) at the same time.

An example of a surgical stapler suitable for endoscopic applications is described in published U.S. patent application Pub. No. 2004/0232196 A1, entitled, "Surgical stapling instrument having separate distinct closing and firing systems," the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling actions avoid complications that may arise when performing such actions sequentially with different surgical tools that respectively only sever or staple.

Motor-driven endocutters are known in the art. In such devices, a motor powers the cutting and fastening action of the instrument. It is also known to use an on-board battery, located in the handle of the instrument, to power the motor. Published U.S. patent application Pub. No. 2007/0175952 A1, entitled "Motor-driven surgical cutting and fastening instrument with loading force feedback," the disclosure of which is herein incorporated by reference in its entirety, describes one such motor-driven surgical instrument.

SUMMARY

In one general aspect, the present invention is directed to a motor-driven surgical cutting and fastening instrument. According to various embodiments, the instrument may comprise an end effector, a shaft connected to the end effector, and handle connected to the shaft. The end effector may comprise a cutting instrument that, when actuated, longitudinally traverses the end effector to cut tissue clamped in the end effector. The handle may comprise an electric motor for actuating the cutting instrument and a motor control circuit for controlling the motor. The motor control circuit may comprise a power source connected to the motor for electrically powering the motor and a current control circuit, connected to the power source, for varying the current supplied to the motor from the power source. The current control circuit may vary the current supplied to the motor, and consequently, the output torque supplied by the motor, such that the motor has at least (i) a first, low power operational mode for a first portion of a cutting stroke cycle of the cutting instrument, and (ii) a second, high power operational mode for a second portion the cutting stroke cycle of the cutting instrument.

That way, for example, according to various embodiments, the motor can start out at a low power mode at the beginning of the cutting stroke to provide a soft start quality. After the initial soft start, the motor can ramp up to full power for the majority of the cutting stroke, but then transition to a lower power mode before and shortly after the cutting reverses direction. In addition, the motor may transition from a high power mode to a low power mode before the cutting instrument reaches its final, or home, position when it is being retracted. According circuit configurations for controlling the current supplied to the motor are provided.

In addition, according to various embodiments, the motor control circuit may actively brake the motor before it reverses direction. For example, the motor control circuit may remove power supplied to the motor just prior to the point in time when the cutting instrument is to reach its end-of-stroke position and the motor reverses direction. In various embodiments, the motor control circuit may comprise a memory that stores data regarding the cartridge loaded in the end effector, from which data the motor control circuit can determine when in the cutting stroke the motor should be actively braked. In other embodiments, the motor control circuit may not include any integrated circuits. In such embodiments, an interface between the end effector and the cartridge may complete an electrical circuit that is connected to the motor control circuit and that has characteristics (e.g., resistance) that control when the motor is actively braked by the motor control circuit.

These and other benefits of the present invention will be apparent from the description below.

FIGURES

Various embodiments of the present invention are described herein by way of example in conjunction with the following figures, wherein:

FIGS. 1, 2, and 24 depict a surgical instrument with an articulatable end effector according to various embodiments of the present invention;

Figure 12:
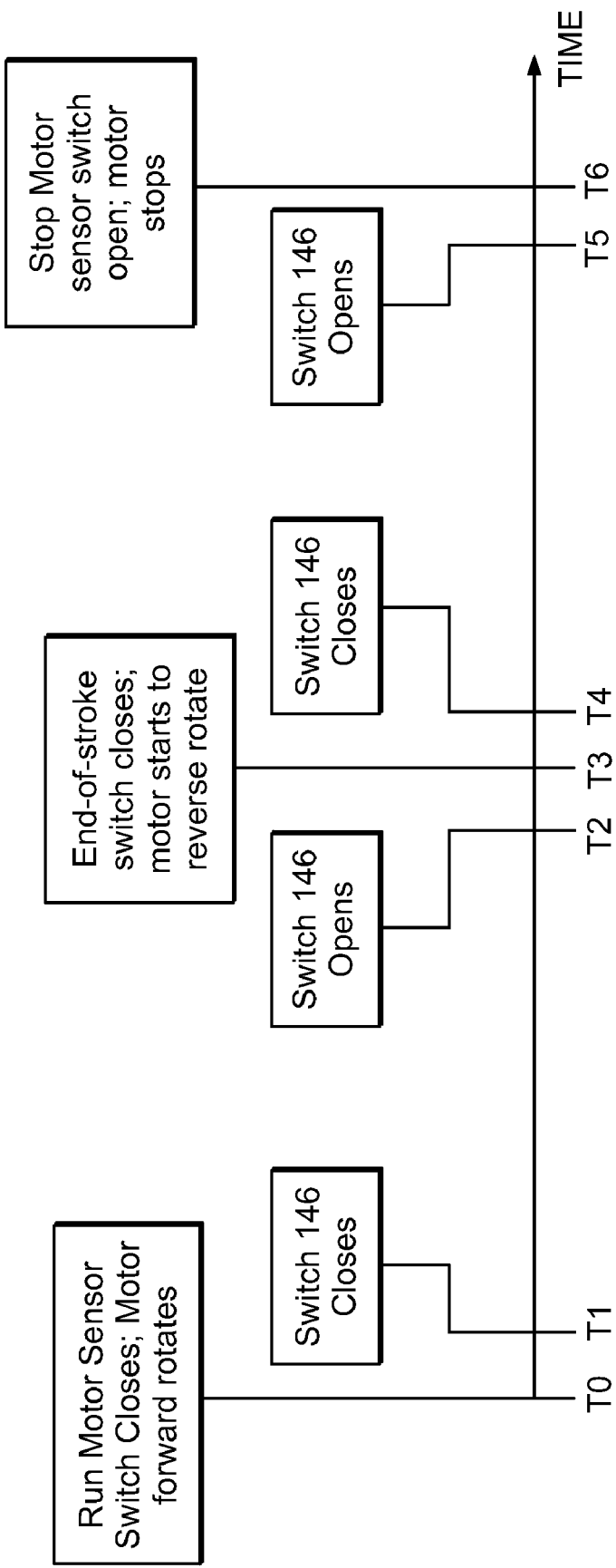
Figure 19:
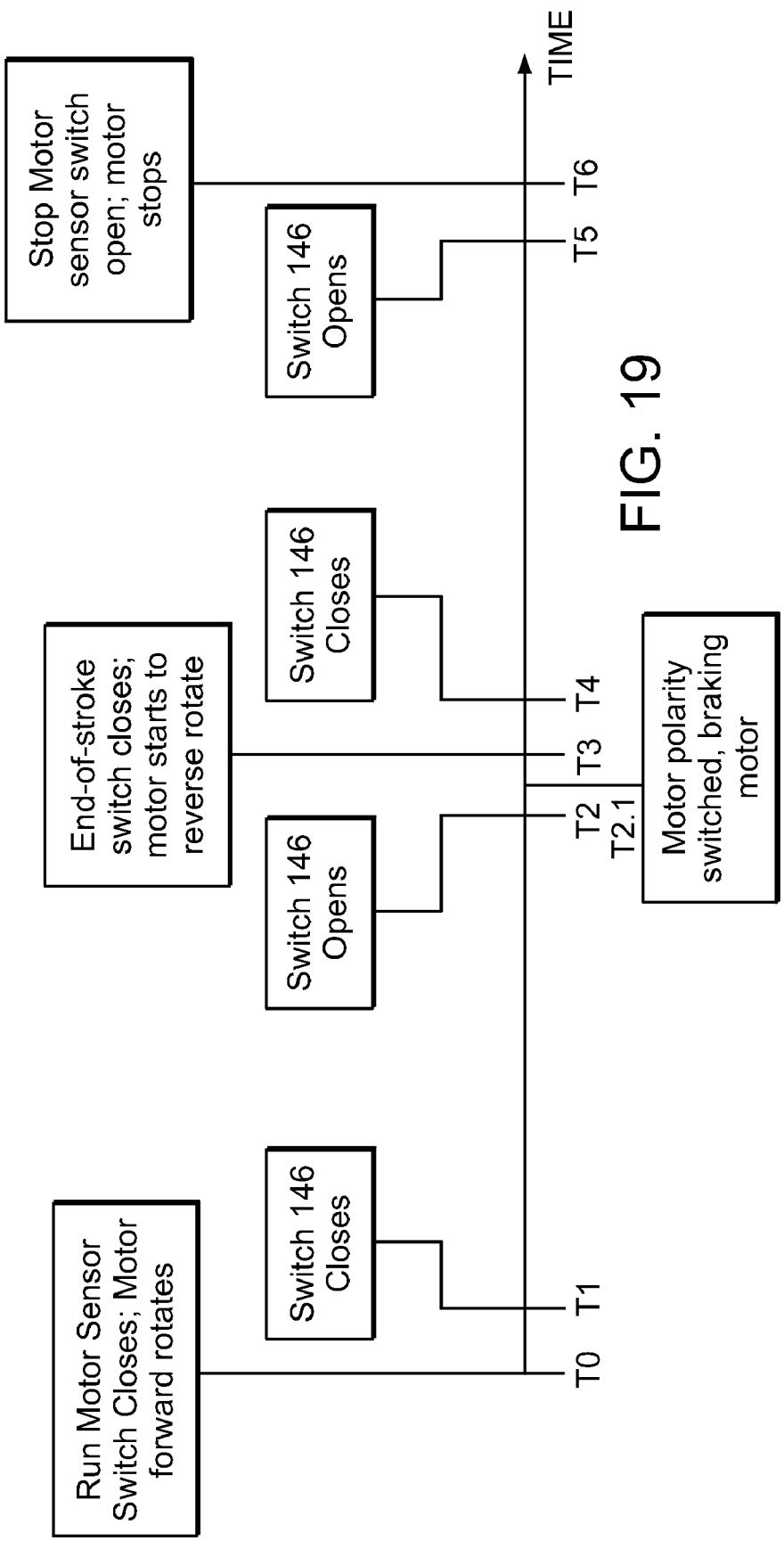
Figure 20:
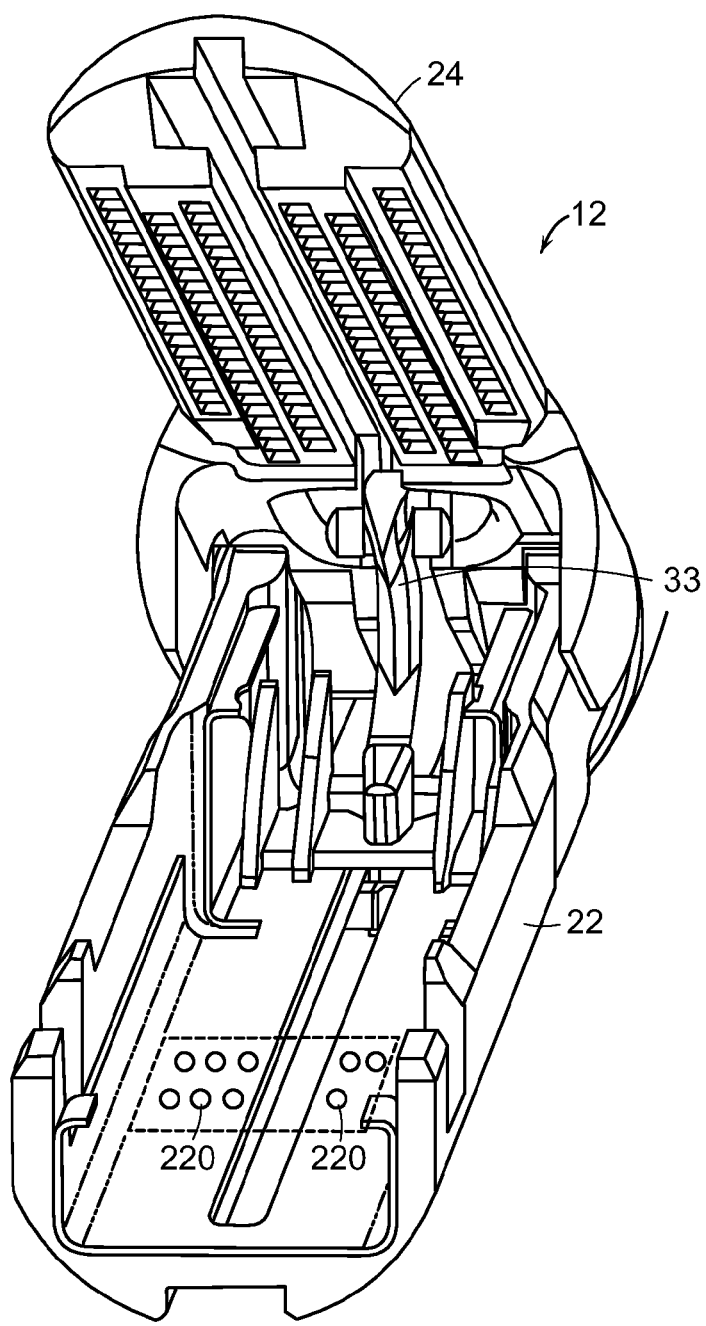
Figure 21:
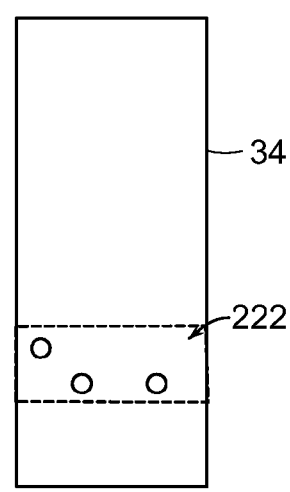
Figure 23:
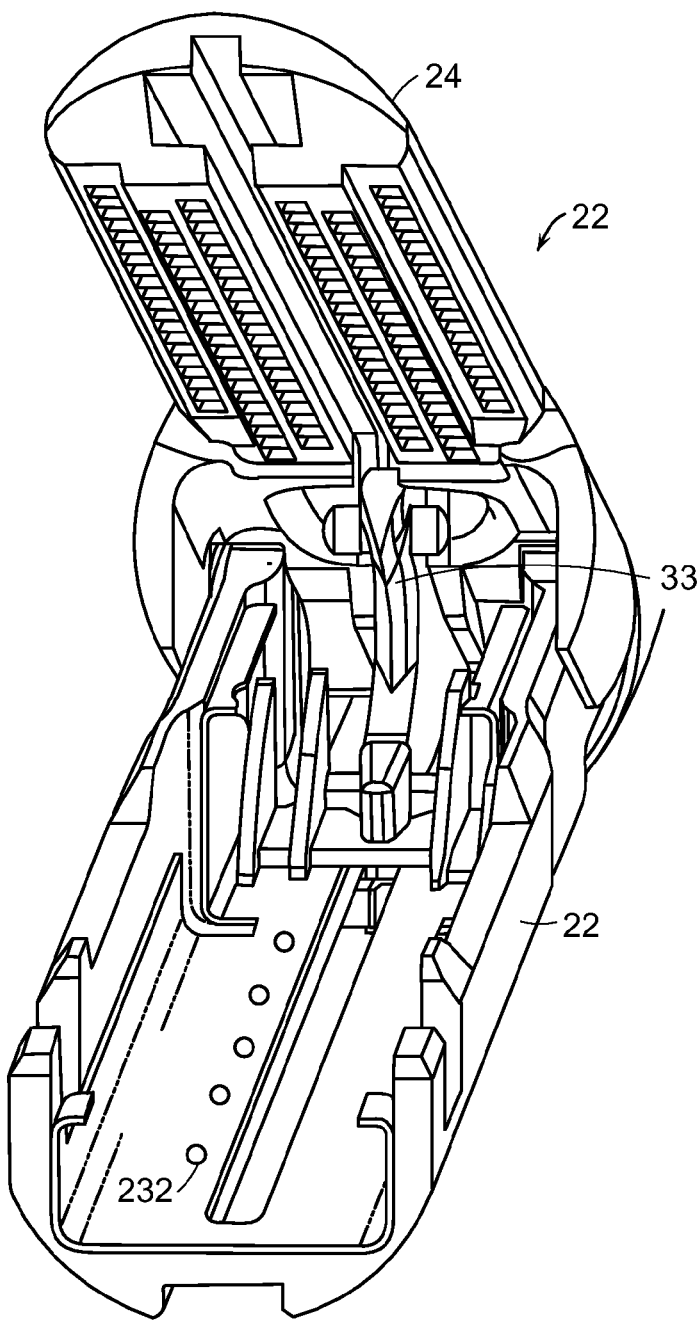
Figure 22:
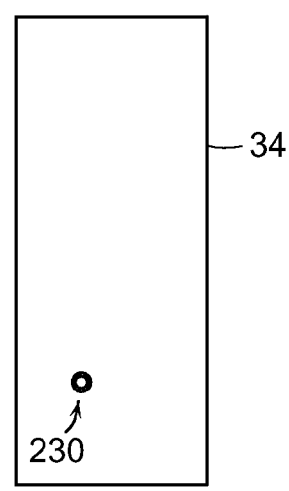

FIGS. 11, 13-18, and 25 are diagrams of motor control circuit according to various embodiments of the present invention;

FIGS. 12 and 19 are timing diagrams illustrating operation of the instrument according to various embodiments of the present invention;

FIGS. 20 and 23 are diagrams of the end effector, without a cartridge, according to various embodiments of the present invention; and FIGS. 21-22 are diagrams of a replaceable cartridge according to various embodiments of the present invention.

DESCRIPTION

Figure 1:
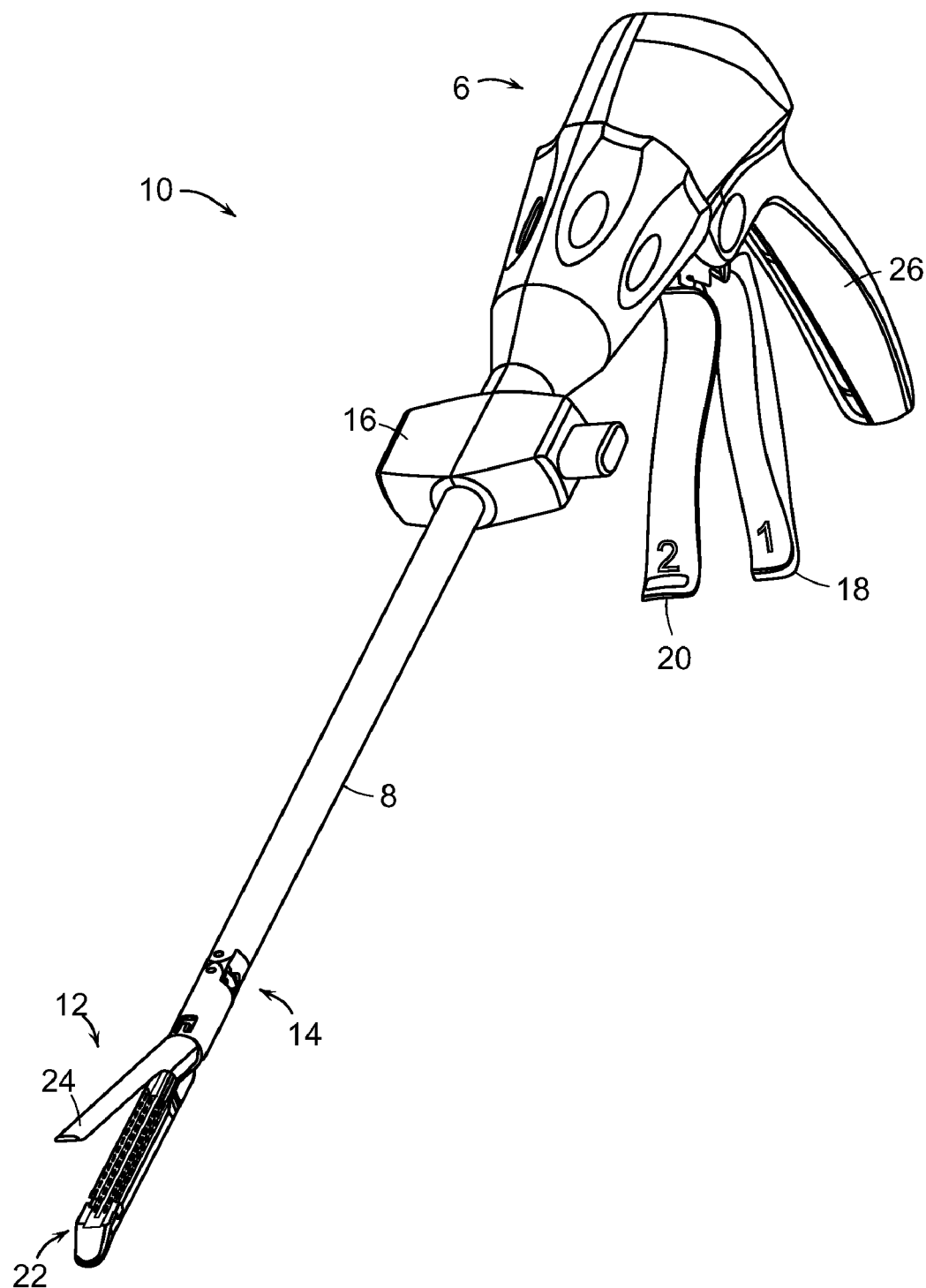
Figure 2:
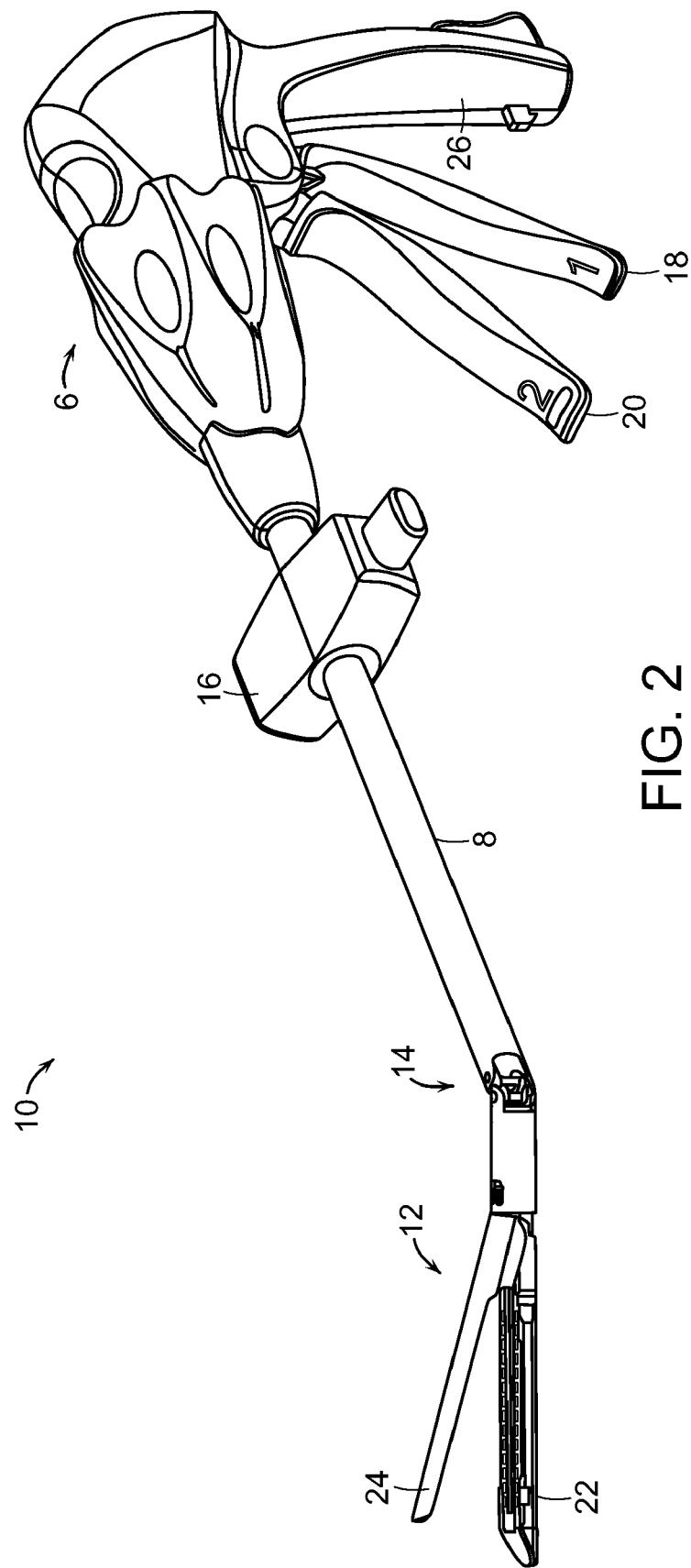

FIGS. 1 and 2 depict a motor-driven surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that the invention is not so limited and that according to other embodiments of the present invention, the instrument may be a non-endoscopic surgical cutting and fastening instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. More details regarding RF devices may be found in U.S. Pat. No. 5,403,312 and commonly assigned U.S. patent application Ser. No. 12/031,573, entitled "Surgical cutting and fastening instrument having RF electrodes, filed Feb. 14, 2008, both of which are incorporated by reference in their entirety.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in published U.S. patent application Pub. No. 2007/0158385 A1, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures, when the anvil 24 is in its clamped position, effective stapling and severing of tissue clamped in the end effector 12. The handle 6 includes a downwardly extending pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

In operational use, the closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, as disclosed in published U.S. patent application Pub. No. 2007/0175955, entitled "Surgical cutting and fastening instrument with closure trigger locking mechanism," which is incorporated herein by reference in its entirety.

Figure 3:
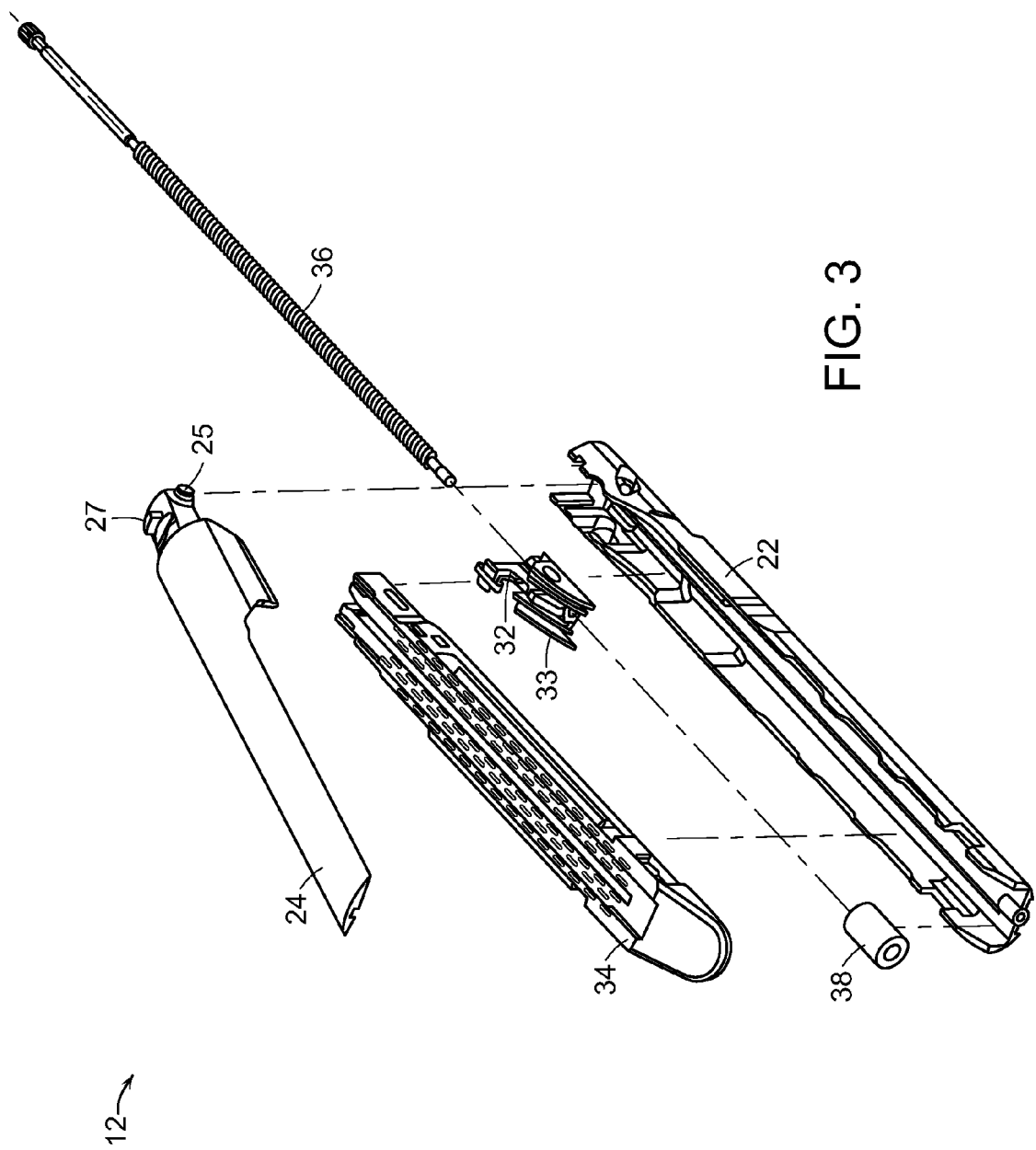
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22 between open and closed positions, respectively. The anvil 24 may also include a tab 27 at its proximate end that is inserted into a component of the mechanical closure system (described further below) to open and close the anvil 24. When the closure trigger 18 is actuated, that is, drawn in by a user of the instrument 10 toward the pistol grip portion 26, the anvil 24 may pivot about the pivot point 25 into the clamped or closed position. If clamping of the end effector 12 is satisfactory, the operator may actuate the firing trigger 20, which causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "Surgical stapling instrument incorporating an E-beam firing mechanism," which is incorporated herein by reference in its entirety, provides more details about such two-stroke cutting and fastening instruments. In various embodiments, the sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTROSURGICAL HEMOSTATIC DEVICE WITH RECESSED AND/OR OFFSET ELECTRODES" to Yates et al., which are incorporated herein by reference in their entirety, disclose an endoscopic cutting instrument that uses RF energy to seal the severed tissue. Published U.S. patent application Pub. No. 2007/0102453 A1 to Jerome R. Morgan, et al. and published U.S. patent application Pub. No. 2007/0102452 A1 to Frederick E. Shelton, IV, et al., which are also incorporated herein by reference, disclose endoscopic cutting instruments that use adhesives to fasten the severed tissue. Accordingly, although the description herein refers to cutting/stapling operations and the like below, it should be recognized that this is an exemplary embodiment and is not meant to be limiting. Other tissue-fastening techniques may also be used.

Figure 4:
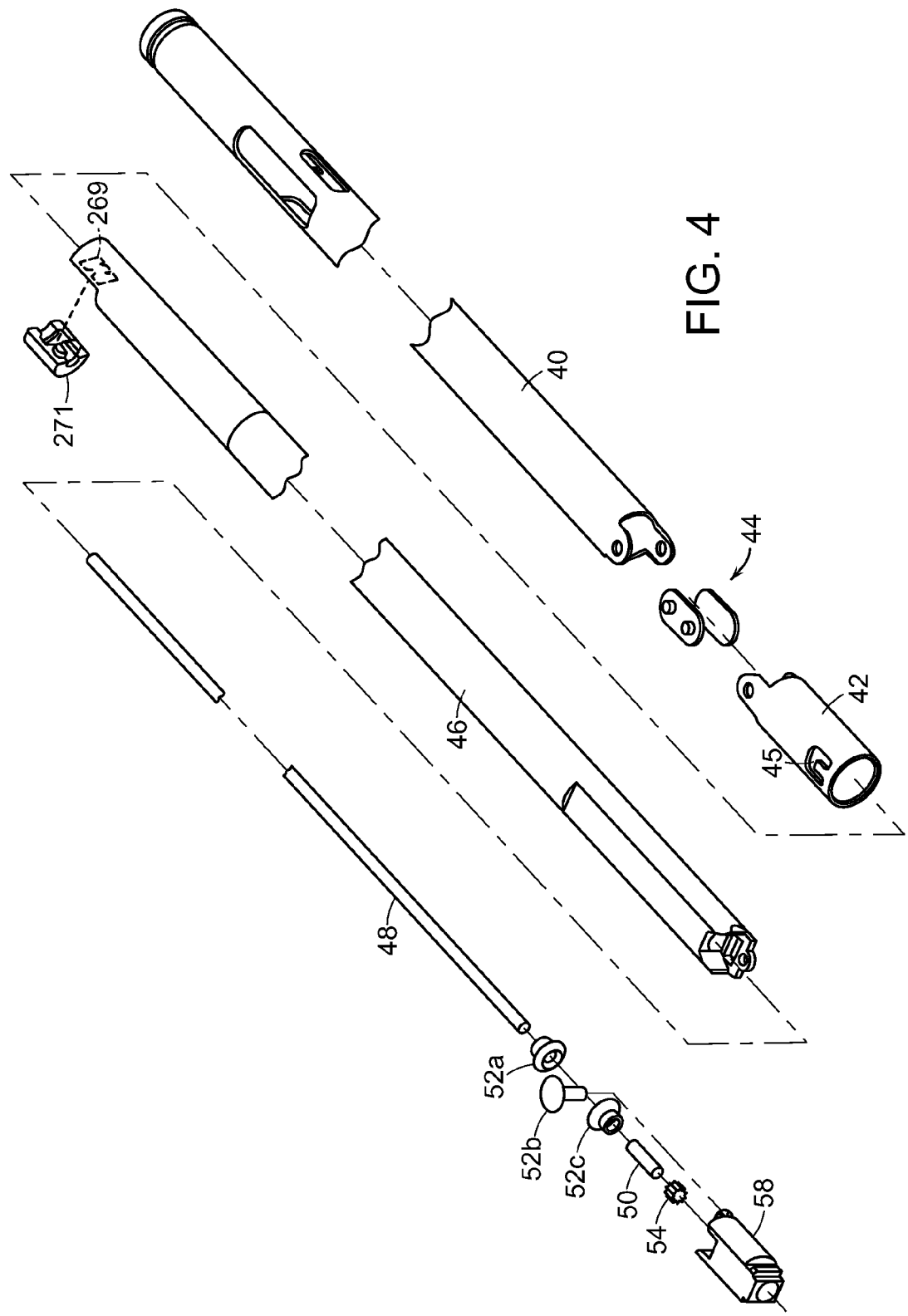
Figure 5:
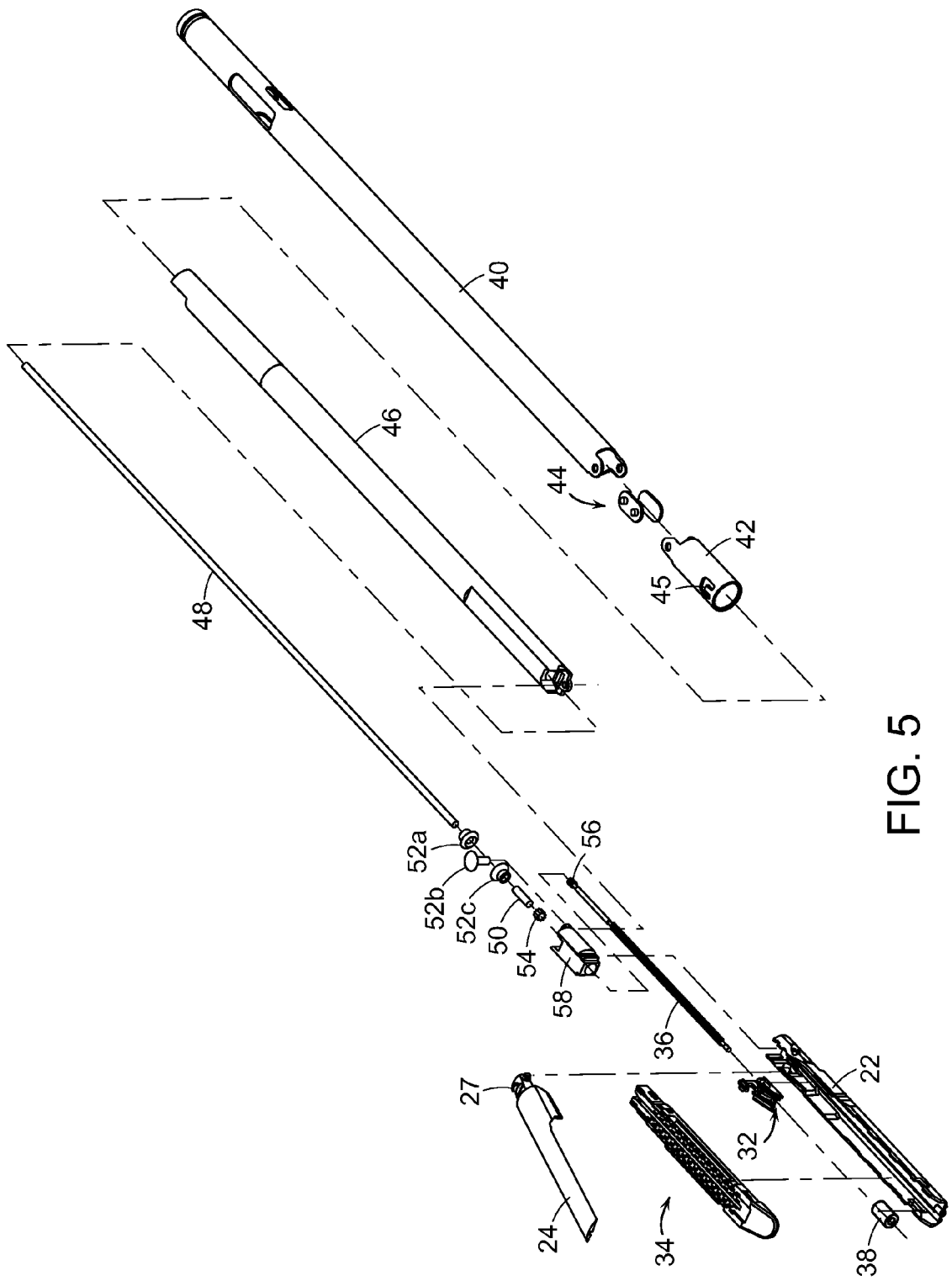
Figure 6:
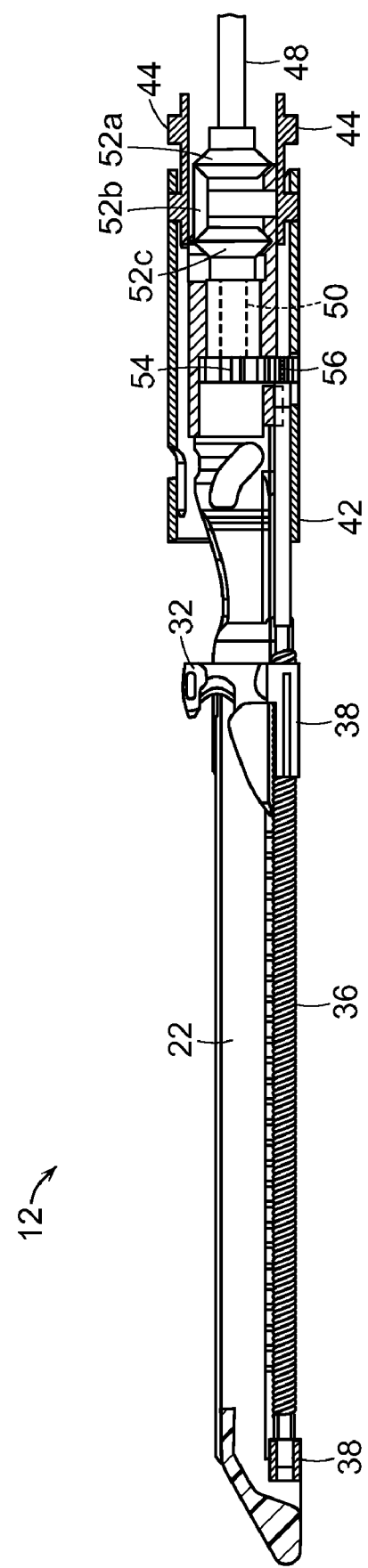
FIG. 6 is a side view of the end effector according to various embodiments of the present invention.
Figure 7:
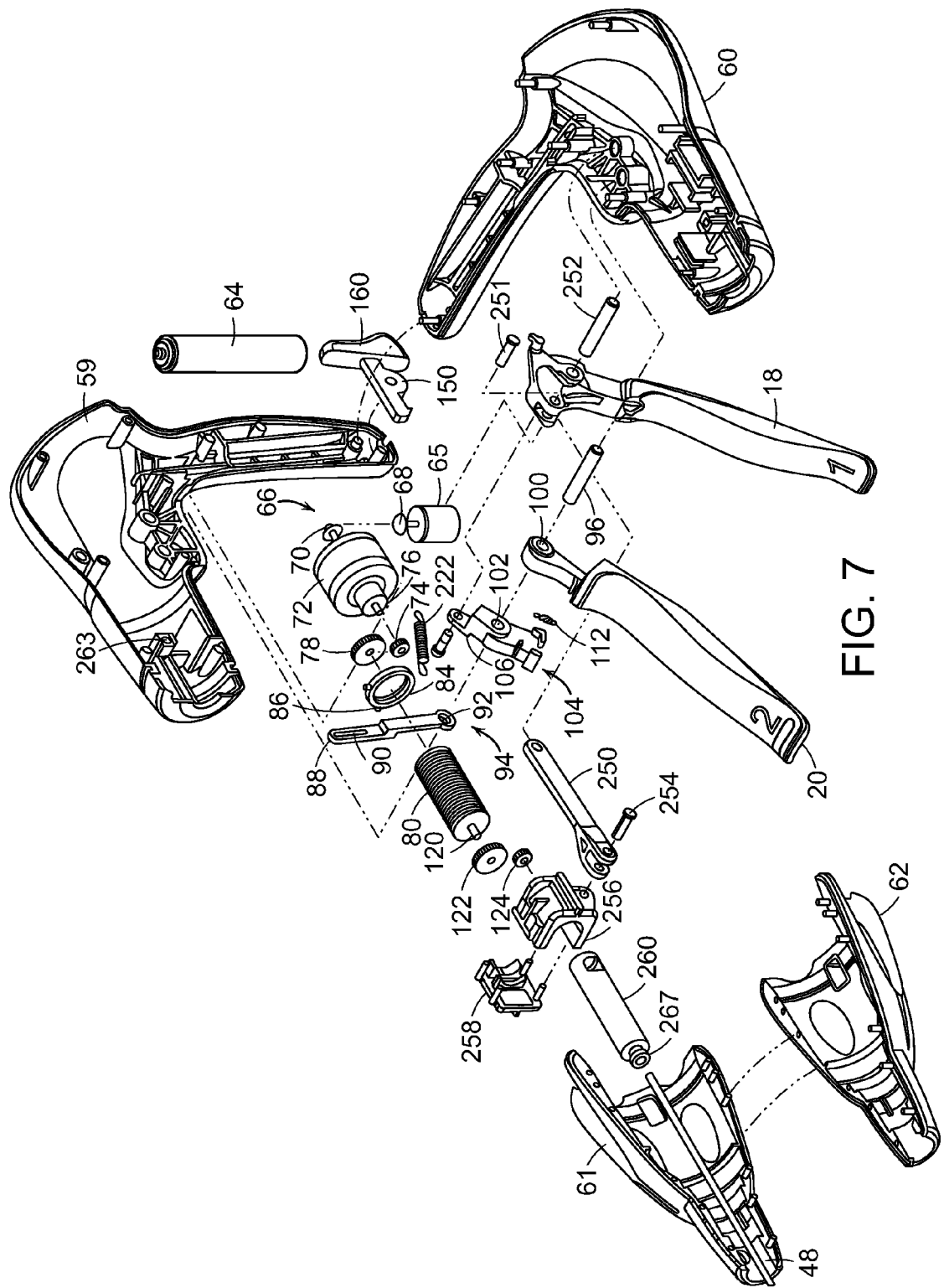
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

In addition, according to various embodiments, the instrument 10 may comprise a cutting instrument position sensor 150 that senses the position of the cutting instrument 32 within the staple channel 22. In one embodiment, the cutting instrument position sensor 150 may comprises an encoder positioned to sense rotation of the helical screw shaft 36, or any other drive shaft or gear whose rotation is related to the position of the knife 32 in the end effector 12. Because the rotation of the shaft 36 or other drive shafts/gears is proportional to the movement of the cutting instrument 32 along the length of the channel 22, the signal generated by the encoder 150 is also proportional to the movement of the cutting instrument 32 in the channel 22.

FIGS. 7-10 illustrate an exemplary embodiment of a motor-driven endocutter. The illustrated embodiment provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower sidepieces 59, 60 and exterior upper side pieces 61, 62 that fit together to form, in general, the exterior of the handle 6. A battery (or "power source" or "power pack") 64, such as a Li ion battery, may be provided in the pistol grip portion 26 of the handle 6. The battery 64 powers an electric motor 65 disposed in an upper portion of the pistol grip portion 26 of the handle 6. According to various embodiments, a number of battery cells connected in series may be used to power the motor 65. In addition, the power source 64 may be replaceable and/or rechargeable.

The motor 65 may be a DC brushed driving motor having a maximum rotation of, approximately, 25,000 RPM. In other embodiments, the motor 65 may include a brushless motor, a cordless motor, a synchronous motor, a stepper motor, or any other suitable electric motor. The motor 64 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72, and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and complete the circuit used to power the motor 65. When the sensor 110 is a variable resistor or the like, the current supplied to the motor 65, and hence the output torque of the motor 65, may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation. In other embodiments, the sensor 110 may be an on-off type switch. In such an embodiment, when the firing trigger 20 is retracted, the sensor switch 110 is closed, thereby completing the circuit used to power the motor 65.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to remove thereby force from the sensor 100, to stop thereby the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130 may be part of the circuit used to control the motor 65. When the reverse motor sensor is activated, the motor control circuit may reverse the direction of the motor 65, thereby withdrawing the knife 32 of the end effector 12 following the cutting operation. The stop motor sensor 142 may be, for example, a normally closed limit switch, and may also be part of the motor control circuit. In various embodiments, it may be located at the proximate end of the helical gear drum 80 so that the ring 84 trips the switch 142 when the ring 84 reaches the proximate end of the helical gear drum 80, indicating that the cutting instrument 32 has reached its proximate (or home or initial) position in the end effector 12.

In operation, when an operator of the instrument 10 pulls back the firing trigger 20, the sensor 110 detects the deployment of the firing trigger 20 and the motor control circuit causes the motor 65 to forward rotate at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which causes the motor control circuit to reverse the direction of the motor 65. This in turn causes the knife 32 to retract, and also causes the ring 84 on the helical gear drum 80 to move back to the proximate end of the helical gear drum 80.

Figure 8:
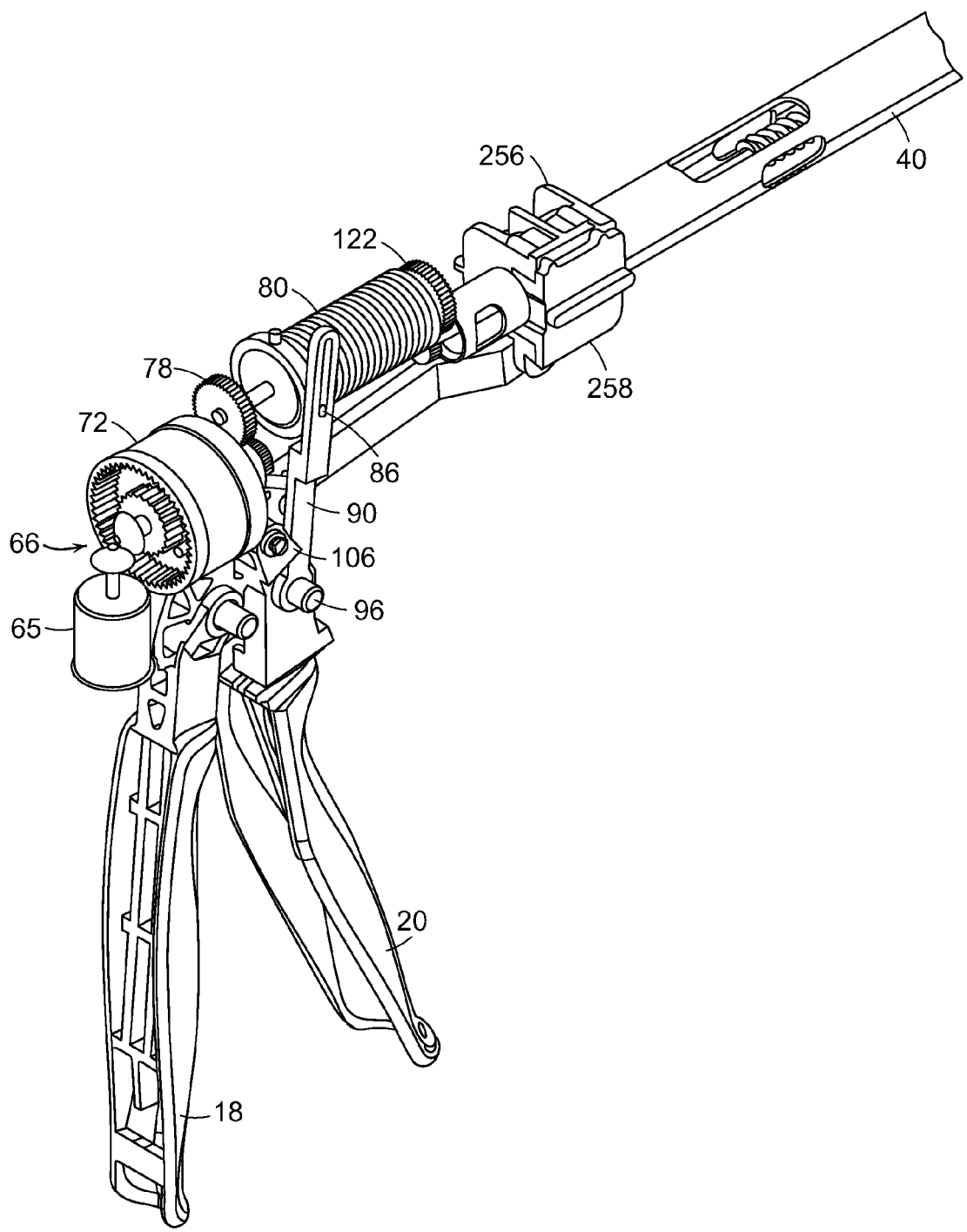
FIGS. 8 and 9 are partial perspective views of the handle according to various embodiments of the present invention.
Figure 9:
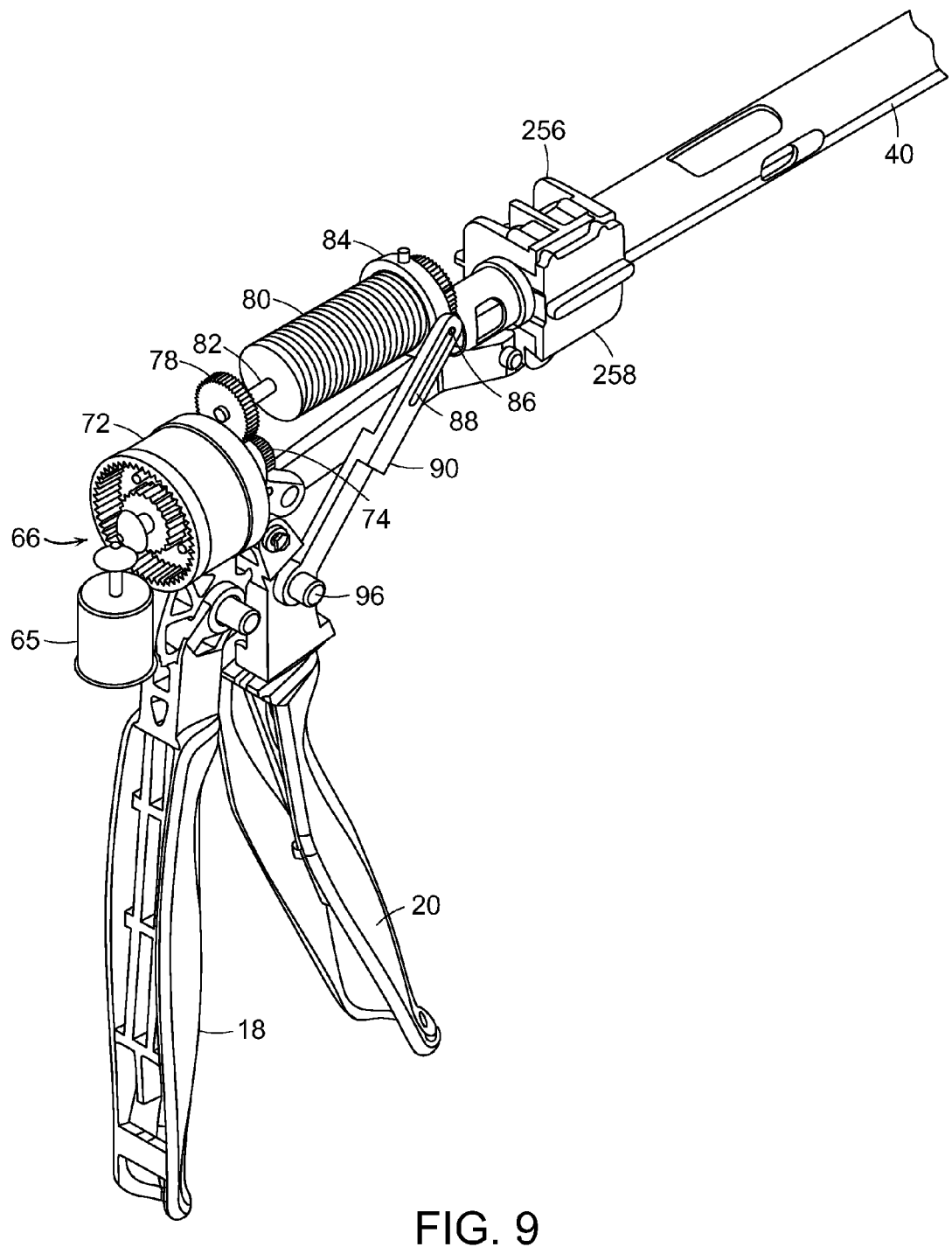
Figure 10:
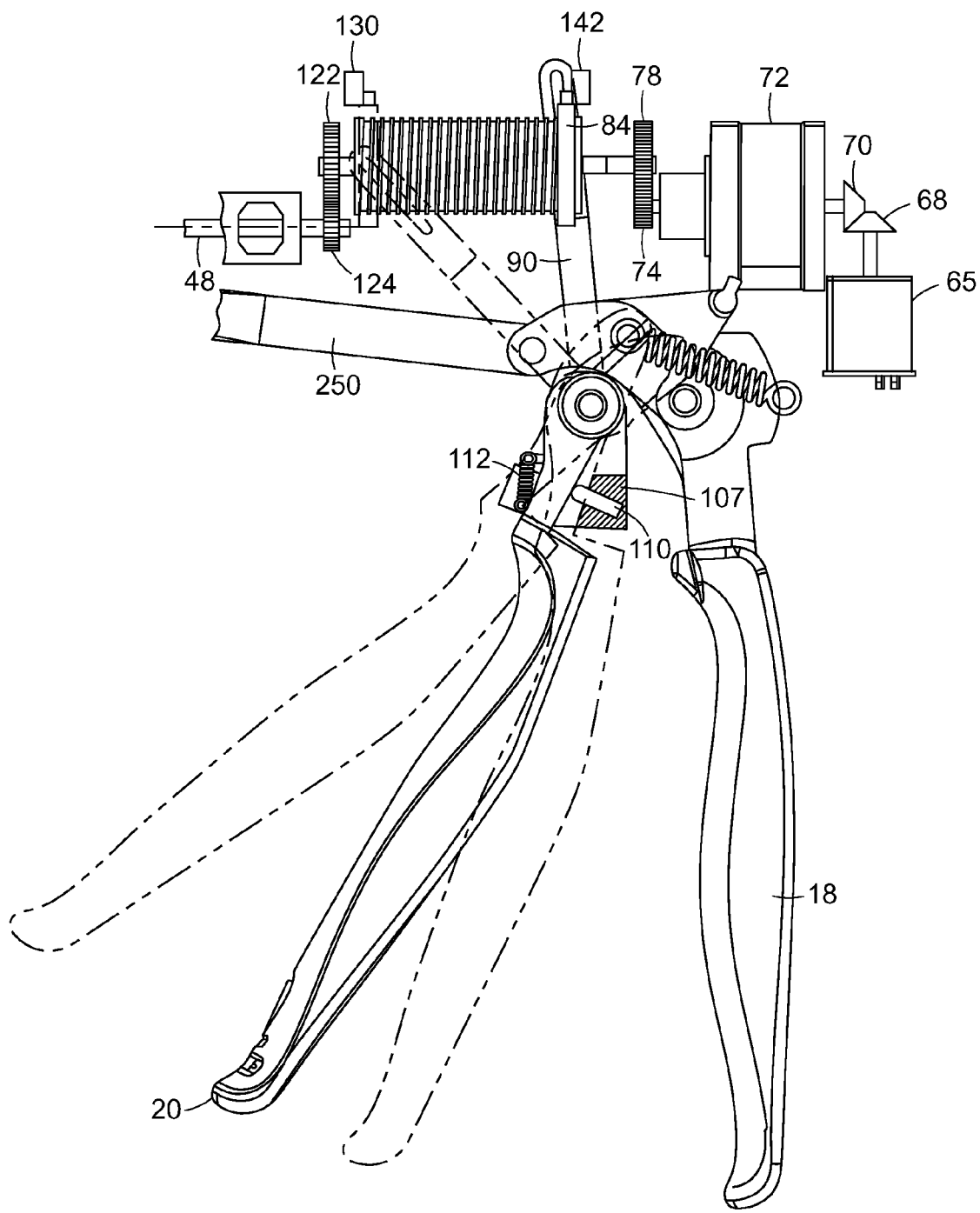
FIG. 10 is a side view of the handle according to various embodiments of the present invention.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower sidepiece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Additional configurations for motorized surgical instruments are disclosed in published U.S. application Pub. No. 2007/0175962 A1, entitled "Motor-driven surgical cutting and fastening instrument with tactile position feedback," which is incorporated herein by reference in its entirety.

Figure 11:
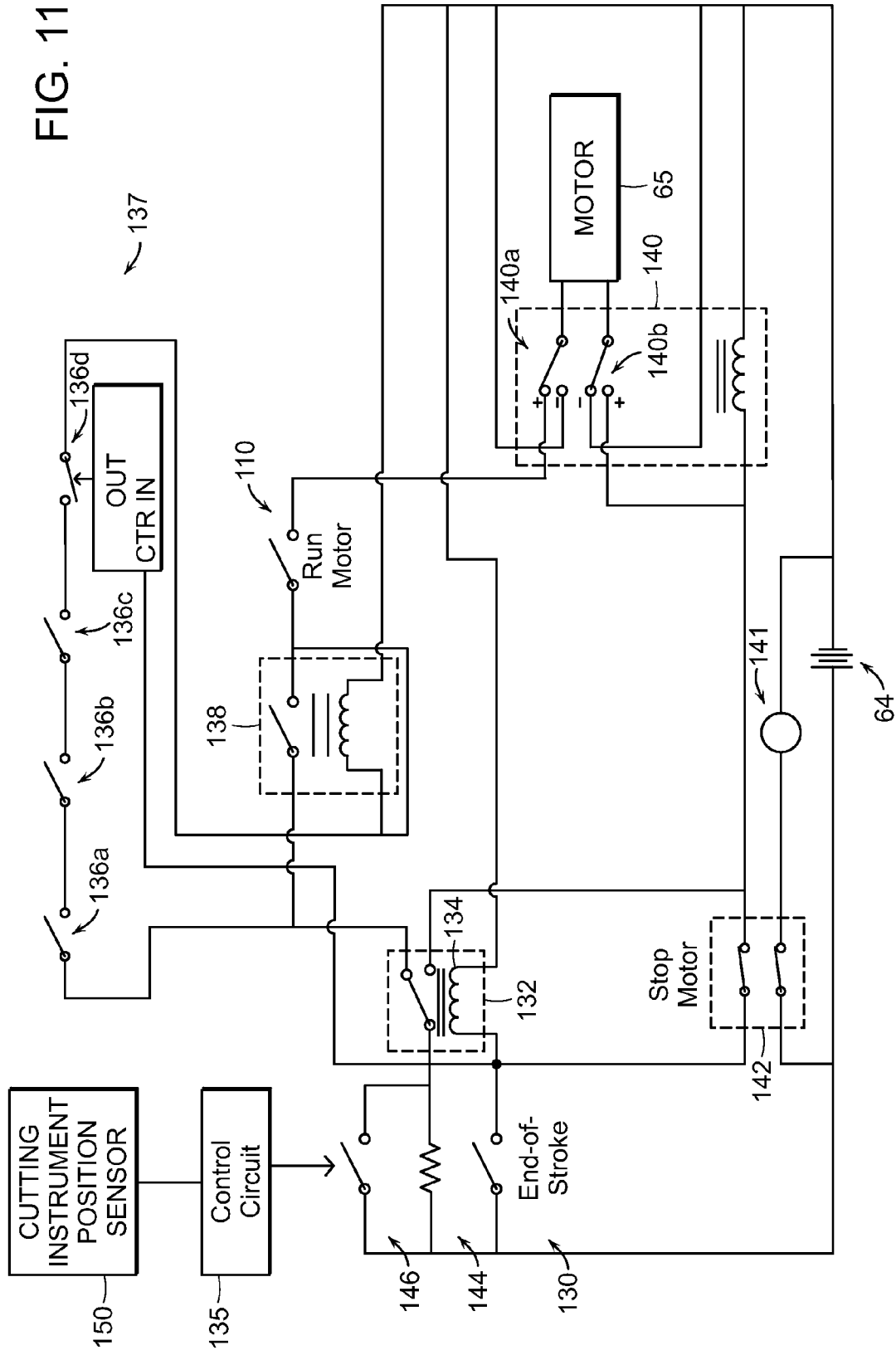

FIG. 11 is a schematic diagram of the motor control circuit according to various embodiments of the present invention. In various embodiments, the motor control circuit may include one of more integrated circuits (ICs), such as, for example, a processor, memory, microcontroller, time circuits, etc. In other embodiments, the motor control circuit may not comprise any ICs. Such a non-IC motor control circuit may be advantageous because it is often difficult, complicated, and expensive to sterilize a surgical instrument including ICs.

When an operator initially pulls in the firing trigger 20 after locking the closure trigger 18, the sensor 110 is activated (or closed, where the sensor 110 is a switch), allowing current to flow therethrough. If the normally open reverse motor sensor switch 130 is open (meaning the end of the end effector stroke has not been reached), current will flow to a single pole, double throw relay 132. When the reverse motor sensor switch 130 is not closed, a coil 134 of the relay 132 will not be energized, so the relay 132 will be in its de-energized state.

As shown in FIG. 11, the circuit may also include a resistive element 144 and a switch 146 connected in parallel, with the paralleled elements connected in series with the relay 132. The resistive element 144 and the switch 146 are also connected to the power source 64. The switch 146 may be controlled by a control circuit 148 that is responsive to the cutting instrument position sensor 150. According to various embodiments, the control circuit 148 may open the switch 146 when the cutting instrument 32 is (i) very near to the beginning of its stroke and (ii) very near to the end of its stroke. For example, the control circuit may open the switch when the cutting instrument 32 is (i) 0.001 inches from the beginning point of its stroke and (ii) 0.001 inches from the end of its stroke, as determined by the cutting instrument position sensor 150. With the switch 146 open, current flows through the resistive element 144, and then through the relay 132, the relay 138, the run motor sensor switch 110, to the motor 65. Current flowing through the resistive element 144 reduces the magnitude of the current delivered to the motor 65, thereby reducing the power delivered by the motor 65. Thus, when the cutting instrument 32 is (i) very near to the beginning of its stroke or (ii) very near to the end of its stroke, the power delivered by the motor 65 is reduced. Conversely, once the cutting instrument 32 moves sufficiently far from its beginning point or end of stroke point, the control circuit 148 may close the switch 146, thereby shorting the resistive element 144, thereby increasing the current to the motor 65, thereby increasing the power delivered by the motor.

According to various embodiments, the electrical circuit further includes lockout sensor switches 136a-d collectively defining an interlock circuit 137 through which current from the relay 132, when de-energized, passes in order for electrical operation of the motor 65 to be initiated. Each lockout sensor switch 136a-d may be configured to maintain an open (i.e., non-conductive) switch state or a closed (i.e., conductive) switch state responsive to the presence or absence, respectively, of a corresponding condition. Any of the corresponding conditions, if present when the instrument 10 is fired, may result in an unsatisfactory cutting and stapling operation and/or damage to the instrument 10. Conditions to which the lockout sensor switches 136a-d may respond include, for example, (a) the absence of the staple cartridge 34 in the channel 22, (b) the presence of a spent (e.g., previously fired) staple cartridge 34 in the channel 22, and (c) an open (or otherwise insufficiently closed) position of the anvil 24 with respect to the channel 22. Other conditions to which the lockout sensor switches 136a-d may respond, such as component wear, may be inferred based upon an accumulated number of firing operations produced by the instrument 10. Accordingly, in various embodiments, if any of these conditions exists, the corresponding lockout sensor switches 136a-d maintain an open switch state, thus preventing passage of the current necessary to initiate operation of the motor 65. Passage of current by the lockout sensors 136a-d is allowed, in various embodiments, only after all of the conditions have been remedied. It will be appreciated that the above-described conditions are provided by way of example only, and that additional lockout sensor switches for responding to other conditions detrimental to operation of the instrument 10 may be provided. It will similarly be appreciated that for embodiments in which one or more of the above-described conditions may not exist or are of no concern, the number of lockout sensor switches may be fewer than that depicted.

As shown in FIG. 11, the lockout sensor switch 136a may be implemented using a normally open switch configuration such that a closed switch state is maintained when the staple cartridge 34 is in a position corresponding to its proper receipt by the channel 22. When the staple cartridge 34 is not installed in the channel 22, or is installed improperly (e.g., mis-aligned), the lockout sensor switch 136a maintains an open switch state. Lockout sensor switch 136b may be implemented using a normally open switch configuration such that a closed switch state is maintained only when an unspent staple cartridge 34 (i.e., a staple cartridge 34 having a sled 33 in the unfired position) is present in the channel 22. The presence of a spent staple cartridge 34 in the channel 22 causes the lockout sensor switch 136b to maintain an open switch state. Lockout sensor switch 136c may be implemented using a normally open switch configuration such that a closed switch state is maintained when the anvil 24 is in a closed position with respect to the channel 22. The lockout sensor switch 136c may be controlled in accordance with a time delay feature wherein a closed switch state is maintained only after the anvil 24 is in the closed position for a pre-determined period of time.

Lockout sensor switch 136d may be implemented using a normally closed switch configuration such that a closed switch state is maintained only when an accumulated number of firings produced by the instrument 10 is less than a pre-determined number. The lockout sensor switch 136d may be in communication with a counter 139 configured for maintaining a count representative of the accumulated number of firing operations performed by the instrument 10, comparing the count to the pre-determined number, and controlling the switch state of the lockout sensor switch 136d based upon the comparison. Although shown separately in FIG. 11, it will be appreciated that counter 139 may be integral with the lockout sensor switch 136d so as to form a common device. Preferably, the counter 139 is implemented as an electronic device having an input for incrementing the maintained count based upon the transition of a discrete electrical signal provided thereto. It will be appreciated that a mechanical counter configured for maintaining the count based upon a mechanical input (e.g., retraction of the firing trigger 20) may be used instead. When implemented as an electronic device, any discrete signal present in the electrical circuit that transitions once for each firing operation may be utilized for the counter 139 input. As shown in FIG. 11, for example, the discrete electrical signal resulting from actuation of the end-of-stroke sensor 130 may be utilized. The counter 139 may control the switch state of lockout sensor switch 136d such that a closed switch state is maintained when the maintained count is less than a pre-determined number stored within the counter 139. When the maintained count is equal to the pre-determined number, the counter 139 causes the lockout sensor switch 136d to maintain an open switch state, thus preventing the passage of current therethrough. It will be appreciated that the pre-determined number stored by the counter 139 may be selectively adjusted as required. According to various embodiments, the counter 304 may be in communication with an external display (not shown), such as an LCD display, integral to the instrument 10 for indicating to a user either the maintained count or the difference between the pre-determined number and the maintained count.

According to various embodiments, the interlock circuit 137 may comprise one or more indicators visible to the user of the instrument 10 for displaying a status of at least one of the lockout sensor switches 136a-d. More details regarding such indicators may be found in published U.S. patent application Pub. No. 2007/0175956, entitled "Electronic lockouts and surgical instrument including same," which is incorporated herein by reference in its entirety. This application also includes example mounting arrangements and configurations for the lockout sensor switches 136a-d.

In the illustrated embodiment, when the lockout sensor switches 136a-d collectively maintain a closed switch state, a single pole, single throw relay 138 is energized. When the relay 138 is energized, current flows through the relay 138, through the run motor switch sensor 110, and to the motor 65 via a double pole, double throw relay 140, thereby powering the motor 65, allowing it to rotate in the forward direction. According to various embodiments, because the output of the relay 138, once energized, maintains the relay 138 in an energized state until relay 132 is energized, the interlock circuit 137 will not function to prevent operation of the motor 165 once initiated, even if one or more of the interlock sensor switches 136a-d subsequently maintains an open switch state. In other embodiments, however, it may be necessary or otherwise desirable to connect the interlock circuit 137 and the relay 138 such that one or more the lockout sensor switches 136a-d must maintain a closed switch state in order to sustain operation of the motor 165 once initiated.

Rotation of the motor in the forward direction causes the ring 84 to move distally and thereby de-actuate the stop motor sensor switch 142 in various embodiments. Because the switch 142 is normally closed, a solenoid 141 connected to the switch 142 may be energized. The solenoid 141 may be a conventional push-type solenoid that, when energized, causes a plunger (not shown) to be axially extended. Extension of the plunger may operate to retain the closure trigger 18 in the retracted position, thus preventing the anvil 24 from opening while a firing operation is in progress (i.e., while the switch 142 is not actuated). Upon de-energization of the solenoid 141, the plunger is retracted such that manual release of the closure trigger 18 is possible.

When the end effector 12 reaches the end of its stroke, the reverse motor sensor 130 will be activated, thereby closing the switch 130 and energizing the relay 132. This causes the relay 132 to assume its energized state (not shown in FIG. 11), which causes current to bypass the interlock circuit 137 and run motor sensor switch 110, and instead causes current to flow to both the normally-closed double pole, double throw relay 140 and back to the motor 65, but in a manner, via the relay 140, that causes the motor 65 to reverse its rotational direction. Because the stop motor sensor switch 142 is normally closed, current will flow back to the relay 132 to keep it energized until the switch 142 opens. When the knife 32 is fully retracted, the stop motor sensor switch 142 is activated, causing the switch 142 to open, thereby removing power from the motor 65, and de-energizing the solenoid 141.

FIG. 12 illustrates a timeline of the operation of the circuit according to various embodiments Assuming the lockout switches 136a-d are in their appropriate state, at time T0 the operator retracts the firing trigger 20, closing the run motor sensor switch 110, causing the motor 65 to forward rotate. At this time, the switch 146 is open, so current flows through the resistive element 144, reducing the current to the motor 65 from time T0 to time T1. At time T1, which the cutting instrument is sufficiently far from its initial position, the switch 146 is closed, thereby shorting the resistive element 144 and supplying increased power to the motor 65. From time T1 to time T2, the motor is in its full power mode with the switch 146 closed. At time T2, as the cutting instrument 32 gets near to the end of its stroke, the switch 146 is opened, thereby reducing the current supplied to the motor 65. Thus, from T2 to T3 the motor 65 is at less than full power.

At time T3, the end-of-stroke sensor switch 130 is closed, causing the motor 65 to reverse rotate. The motor 65 is still in its reduced power state because switch 146 is opened, and the motor 65 remains in its reduced power state until time T4, when the switch 146 is closed because the cutting instrument 32 has moved sufficiently far from its end-of-stroke position. From time T4 to T5 the motor 65 operates at full power retracting the cutting instrument 32. At time T5, as the cutting instrument 32 gets near to its initial (or stop) position, the switch 146 again opens, thereby limiting current to the power 65, thereby reducing the power delivered by the motor 65. At time T6, the stop motor sensor switch 142 is opened, thereby removing current from the motor, causing it to stop rotating.

In such a switching architecture, the motor-driven instrument 10 exhibits a "soft" start quality by limiting the motor's ability to exert full load immediately. The motor 65 is initially in a reduced power mode (from time T0 to time T1), so as to limit the sudden jerking start. In addition, by starting the soft start mode, the likelihood of the motor overpowering the cartridge lockout mechanism is reduced. In addition, reducing the power prior to the knife reaching its end-of-stroke (or distal) position eases reversal of the motor direction.

In other embodiments, the parallel-connected switch 146 and resistive element 144 are connected in different places, but preferably they are always in the current loop regardless of whether the motor 65 is being forward rotated or reverse rotated. In addition, the resistive element 144 may be any type of circuit element or electrical component that provides sufficient resistance. For example, the resistive element 144 could be one or a number of parallel-connected resistors.

Figure 13:
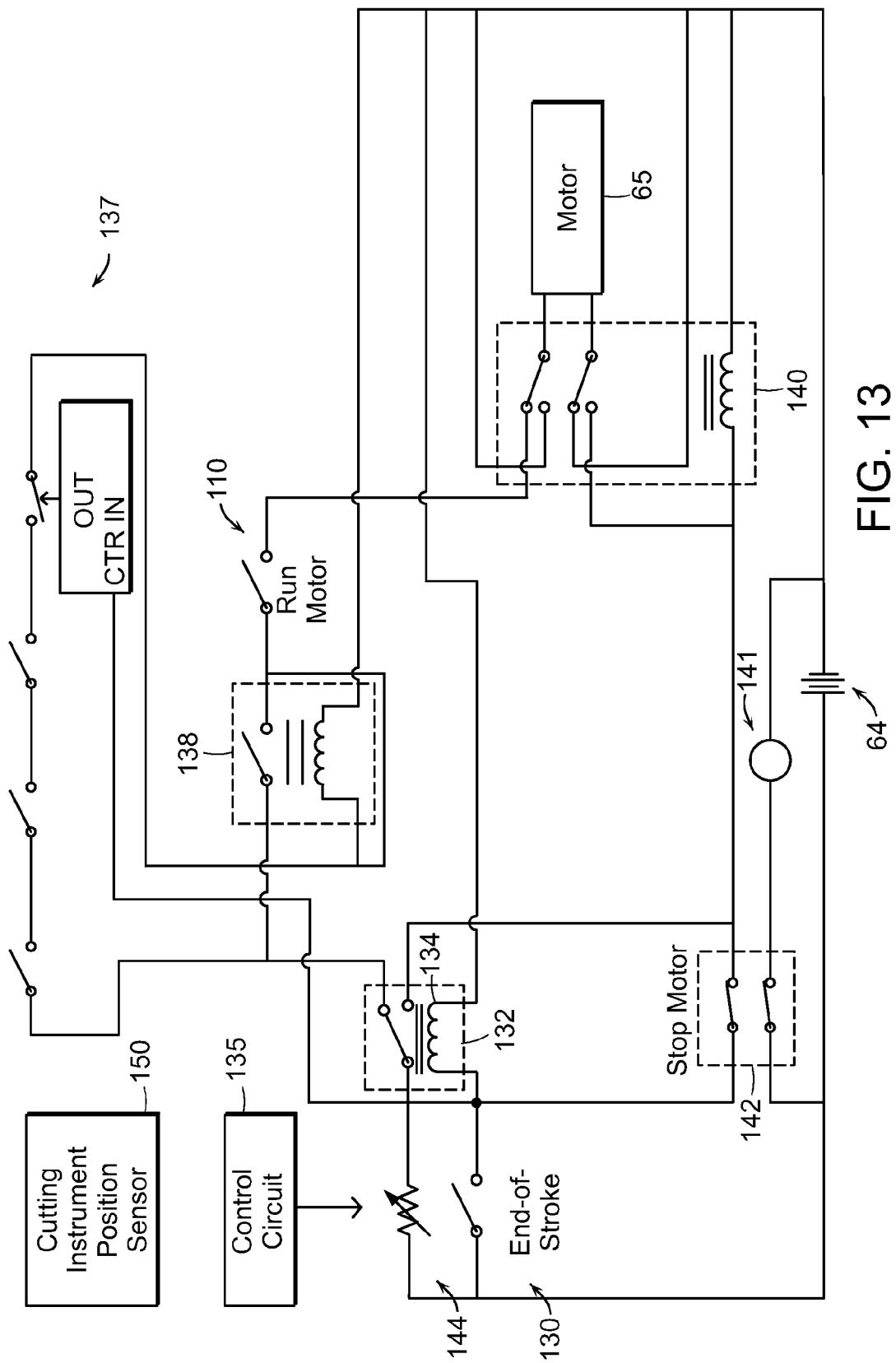
Figure 14:
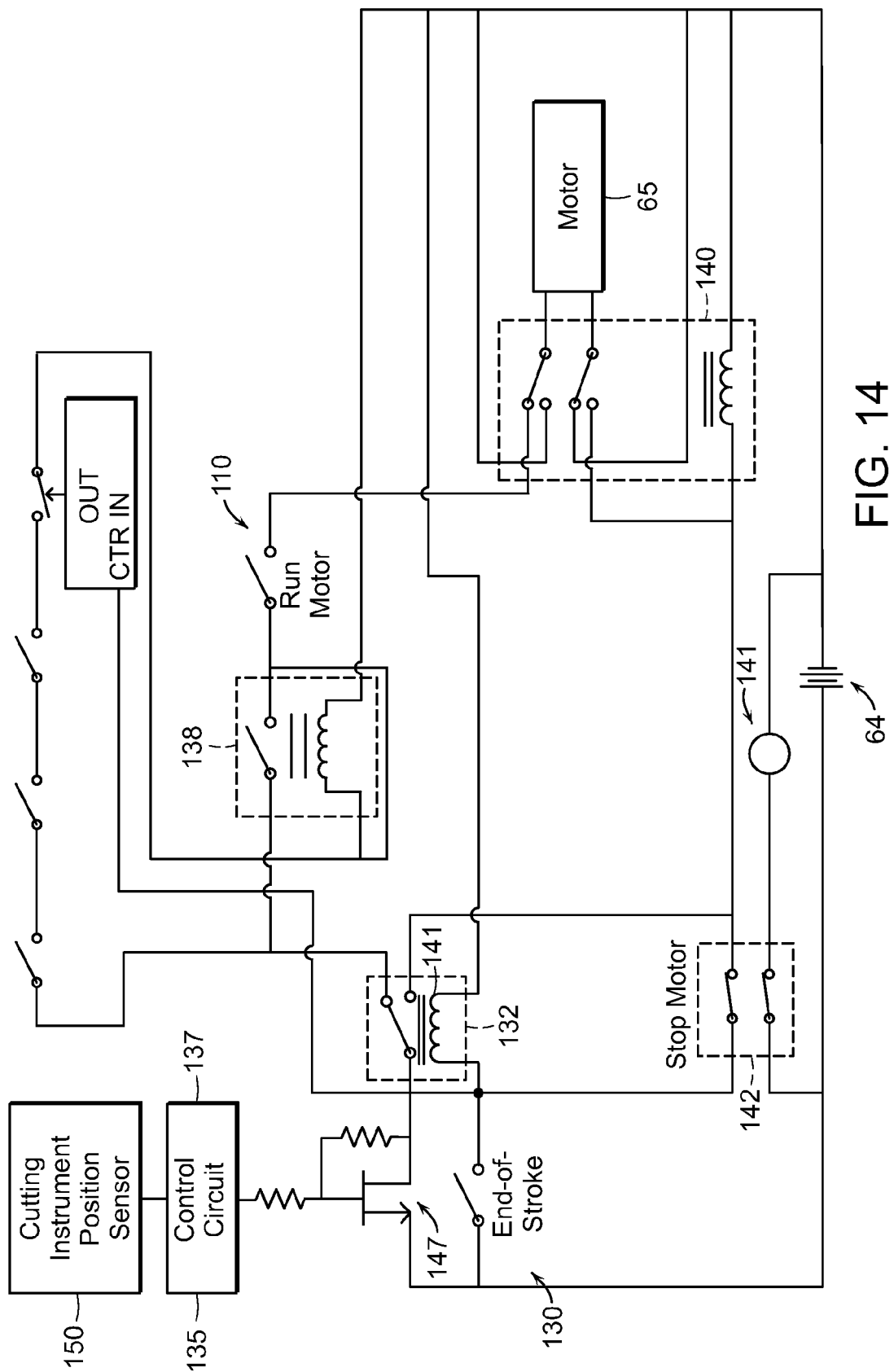

In addition, the resistive element 144 may comprise a variable resistor, as shown in FIG. 13. In such an embodiment, the switch 146 may or may not be used. FIG. 13 shows an embodiment without the switch 146. The control circuit 148 may vary the resistance of the variable resistive element 144 based on the position of the cutting instrument 32, for example. That way, instead of having two power levels for the motor 65, there could be a number of discrete power levels or a continuous range of power levels for the motor 65, depending on the nature of the variable resistive element 144. In various embodiments, the variable resistive element may comprise a string potentiometer or cable position transducer, where, for example, the resistance is related to the position of the knife 32 in the end effector 12. In addition, an active element, such as a transistor, could be used to provide a variable resistance. For example, FIG. 14 illustrates a circuit where a FET 147 is used as a variable resistor to limit the current to the motor 65 in various operational states.

Figure 15:
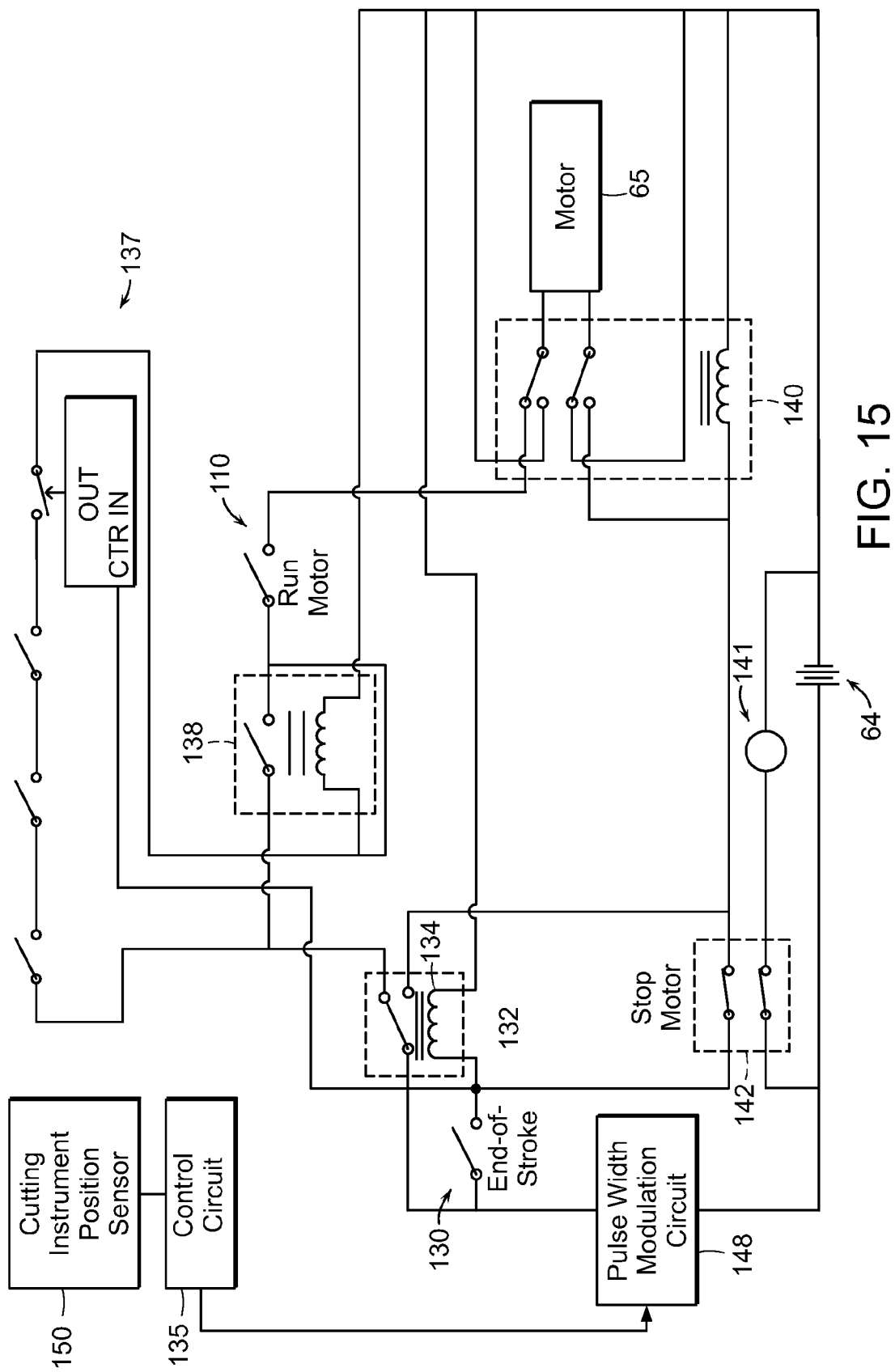
Figure 16:
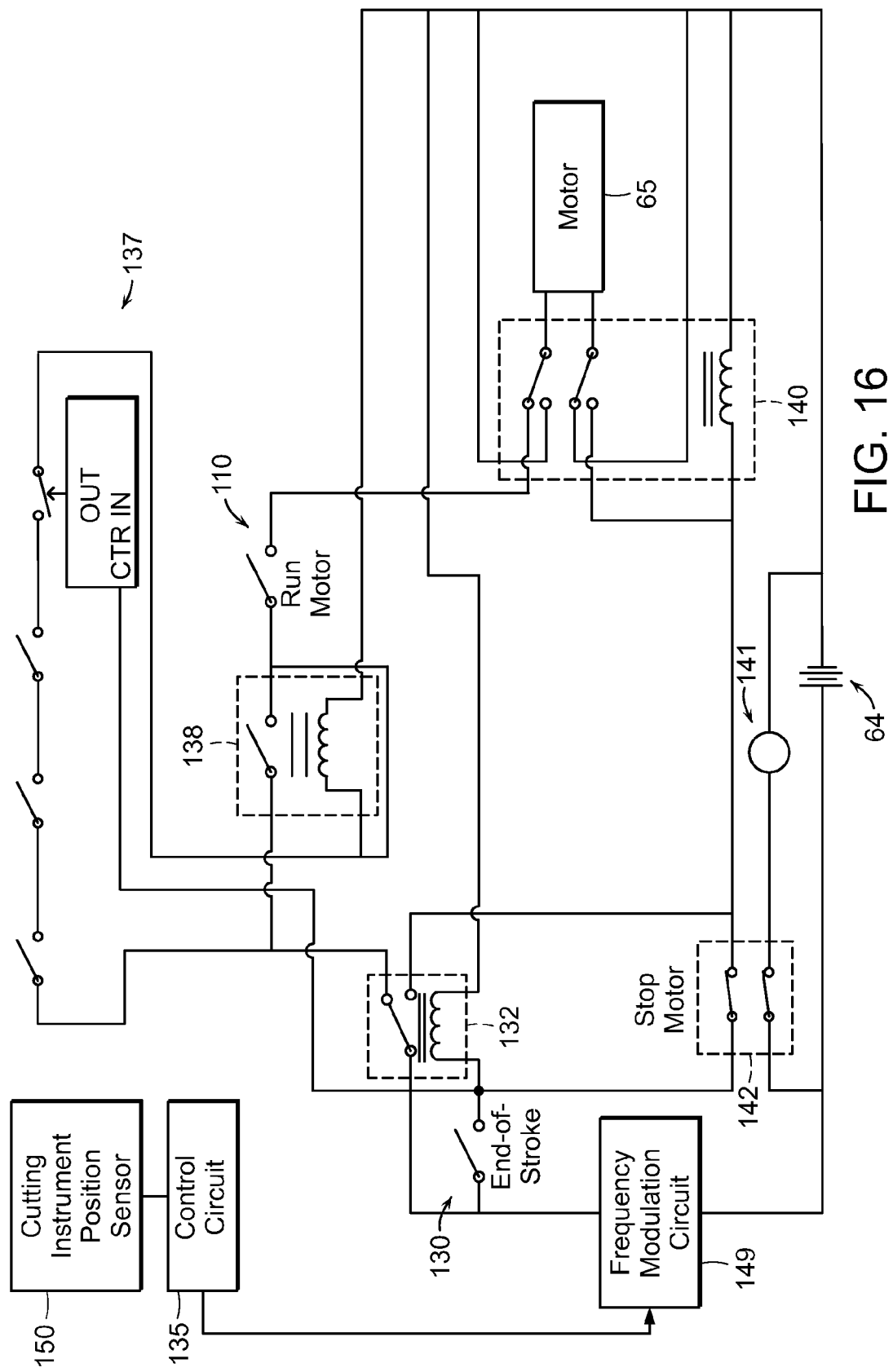

In yet other embodiments, an integrated switch mode controller, such as the UC2637 from Texas Instrument or some other suitable motor drive circuit, could be used to limit the torque and/or speed of the motor 65 at various times during the cutting stroke cycle, such as a "soft" start, within the lockout region, prior to stopping or reversing direction, etc. According to yet other embodiments, as shown in FIG. 15, a pulse width modulation circuit 148 may be used to control the speed of the motor 65 by driving the motor with short pulses. The duration of the pulses may be varied to control the speed of the motor 65; the longer the pulses, the faster the motor turns, and vice versa. Accordingly, short duration pulses may be used when the cutting instrument 32 is initially leaving or returning to its initial position, or approaching or leaving its end-of-stroke position, etc. In addition, in yet other embodiments, a frequency modulation circuit 149, as shown in FIG. 16, may be used to control the speed of the motor 65. In a frequency modulation circuit, the duty cycle of the pulse remains constant, by the frequency of the pulses changes to vary the speed of the motor. Accordingly, low frequency pulses may be used when the cutting instrument 32 is initially leaving or returning to its initial position, or approaching or leaving its end-of-stroke position, etc., and high frequency pulses may be used when greater motor speed is required.

Figure 17:
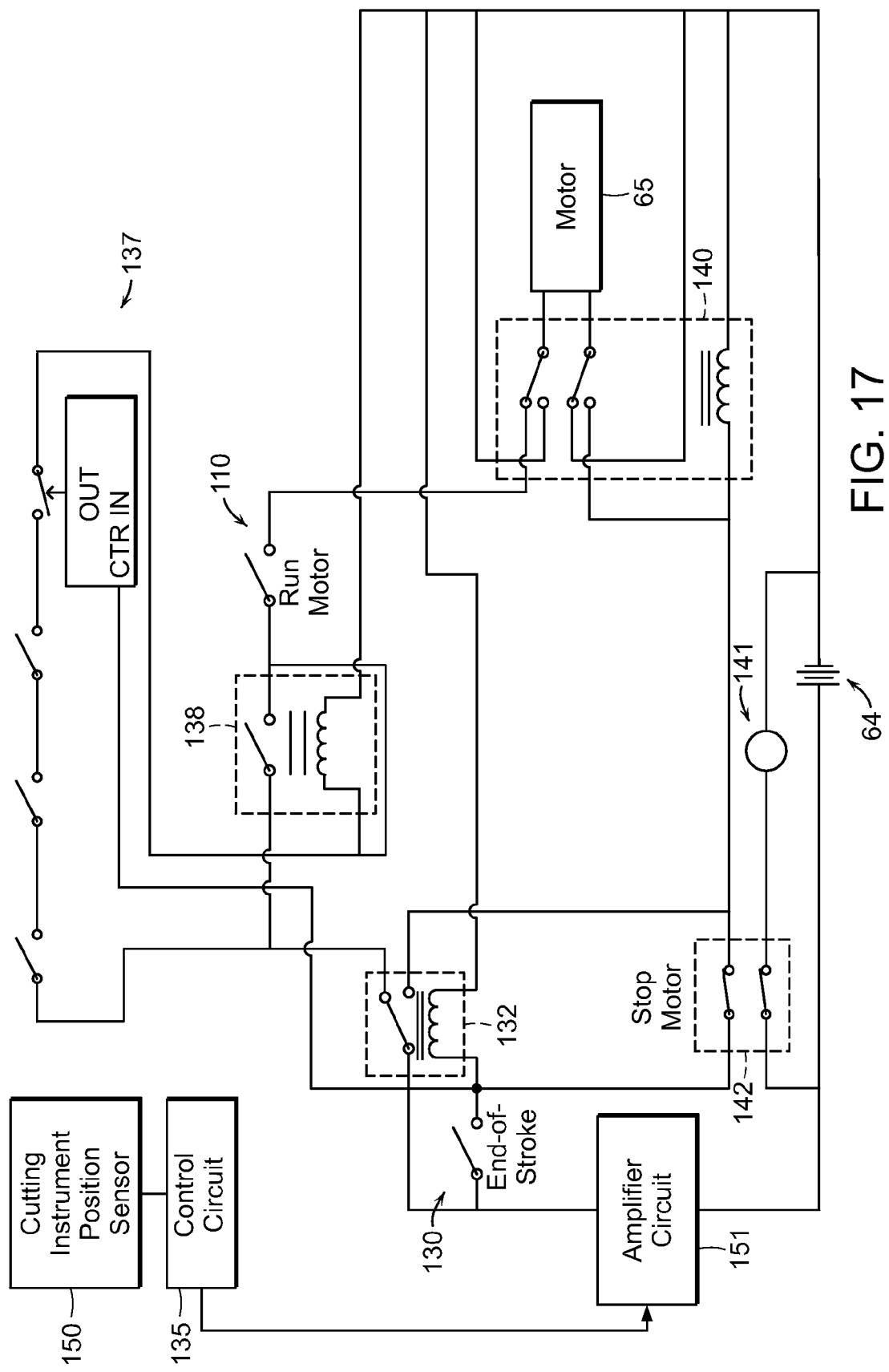

In yet other embodiments, an amplifier circuit 151 may be used to control the speed of the motor 65, as shown in FIG. 17. The amplifier circuit 151 may amplify, for example, the current or voltage applied to the motor 65. According to various embodiments, the amplifier circuit 151 may comprise a Darlington transistor pair or some other suitable transistor-based amplifier circuit.

In other embodiments, rather than an on-off type run motor sensor switch 110, a proportional-type variable resistor sensor could be used instead. In such embodiments, the rate of rotation of the motor 65 would be proportional to the force applied by the operator. The run-motor sensor 110 may provide an open circuit resistance when the firing trigger 20 is not retracted/actuated, and then provide a decreasing resistance as the firing trigger is retracted. Whether the switch 110 comprises an on-off type switch or a variable resistor, if the operator releases the firing trigger 20 during a procedure while the motor is in the forward direction, power to the motor 65 will be eliminated or at least reduced, thereby providing a dynamic braking feature for the instrument 10.

Figure 18:
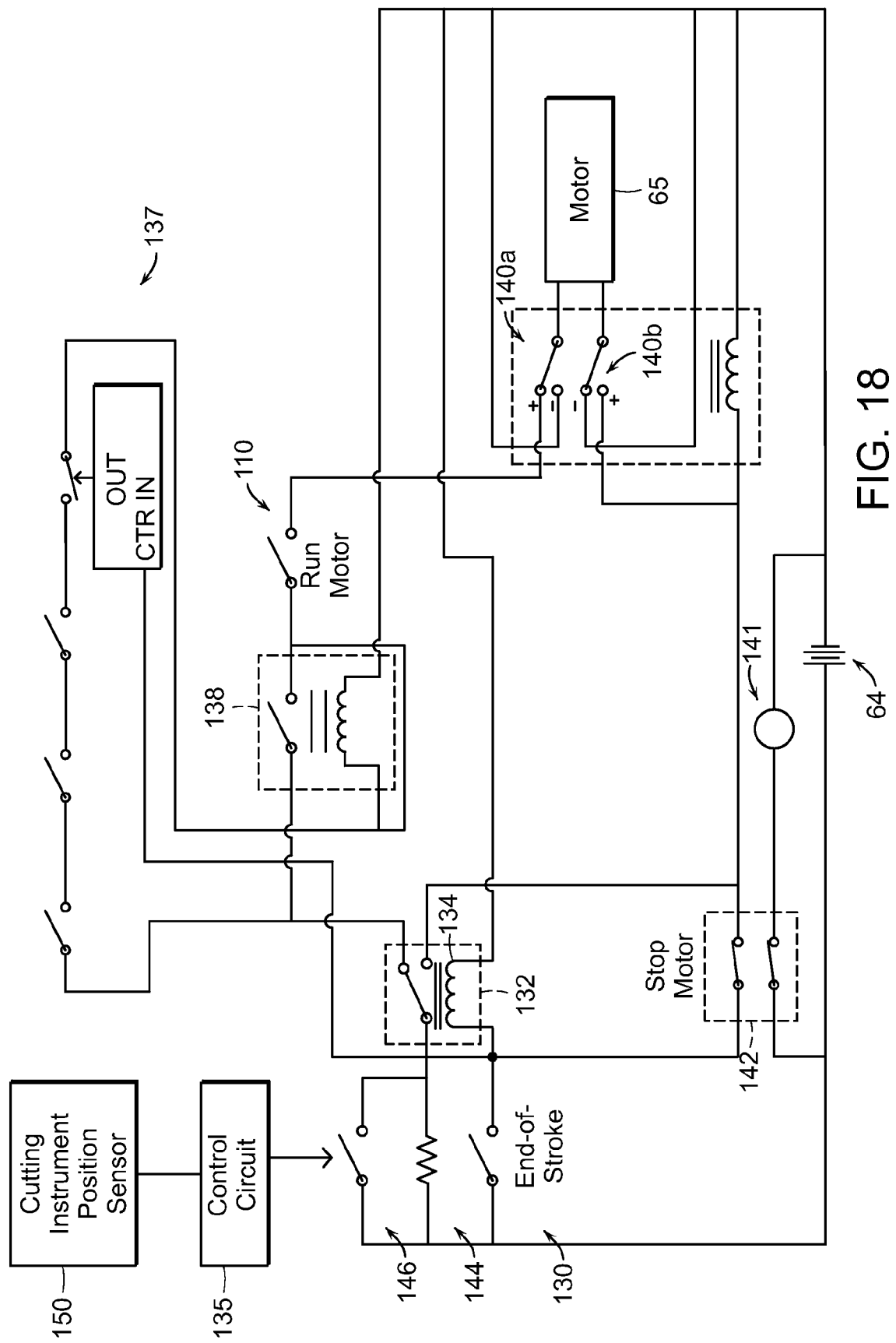

In other embodiments, as shown in FIG. 18, the switches 140a and 140b may be actively controlled, rather than through the relay 140 shown in FIG. 11, for example. In such embodiments, just before the end of the stroke is sensed, one of the switches 140a, 140b may switch polarity so that both switches 140a, 140b are connected to the same polarity terminal for the motor 65 (e.g., either both positive or both negative). This will remove power from the motor 65, causing it to stop. FIG. 18 shows an embodiment where the switches 104a and 140b are both connected to the positive terminal. Then, at about the same time the end-of stroke is sensed or soon thereafter, the other switch 140a, 140b may switch polarity, allowing the motor 65 to rotate in the reverse direction. In the example of FIG. 18, this may be done by switching switch 140a to the negative terminal. Of course, in other embodiments, the switch 140a could be first switched to the negative terminal and then the switch 140b could be switched to the positive terminal. Also, other switching arrangements could be used to temporarily remove power from the motor 65 prior to it switching direction to provide such "active braking." For example, the switches 140a, 140b may still be controlled by an inductive relay, and the circuit may include another switching circuit for actively braking the motor 65.

The active braking could be combined with variable power levels supplied to the motor 65 as described above in connection with FIGS. 11 and 12, for example. FIG. 19 shows a timing diagram that incorporates active braking. At time T2.1, between times T2 and T3, the power may be removed from the motor 65 by switching one of the switches 140a, 104b, for example, thereby braking the motor. Then at time T3, the end-of-stroke switch 130 may be closed and the other switch 140a, 140b may be switched to supply power to the motor 65, but in the reverse direction, as described above.

The control circuit 135 or some other control circuit may control the switching of the switches 140a, 140b. According to various embodiments, the control circuit 135 may comprise a processor and memory. For example, the control circuit 135 may comprise an IC-based microcontroller. The memory may store data indicative of the type of cartridge 34 loaded in the end effector 12. For example, the memory may store data indicative of the length of the cut needed for the cartridge 34. Based on this data, the control circuit 135 can control when the switches 146, 140a, and 140b switch. As the cartridges 34 are often replaceable in certain types of instruments 10, the identifying data may be transmitted to the control circuit 135 by a RFID tag or transponder connected to or associated with the cartridge 34 or by some other means. The RFID signal from the tag may be received by the control circuit 135 and stored in memory. In other embodiments, a transponder associated with the cartridge 34 may send identifying data to the control circuit 135 via one or more inductive links, such as described in published U.S. patent application Pub. No. 2008/0167522, entitled "Surgical instrument with wireless communication between control unit and sensor transponders," which is incorporated herein by reference in its entirety.

According to other embodiments, the control circuit 135 may not contain any integrated circuits. For example, the control circuit 135 may comprise analog timer circuits (e.g., RC-based timer circuits) for controlling the switch timing of the switches 146, 140a-b. According to such an embodiment, the control circuit 135 may receive information about the length of the cut for the particular cartridge 34 being used based on the completion of an electrical circuit when the cartridge 34 is inserted into the channel 22. For example, as shown in FIG. 20, the channel 22 may comprise a number of contact pads 220 positioned to face the lower surface of the cartridge 34 when the cartridge 34 is loaded in the channel 22. The lower surface of the cartridge 34 also may comprise a number of contacts 222, as shown in FIG. 21. The number and positioning of the contacts 222 on the cartridge 34 may identify the type of cartridge. For example, the number and positioning of the contacts 222 may identify the cut length for the cartridge 34. All cartridges of the same cut length would preferably have the same contact pattern; cartridges with different cut lengths would have different contact patterns. The circuit completed when the contacts 222 of the cartridge 34 contact the contacts 220 of the channel 22 may have a number of different resistors, a subset of which are connected in the completed circuit when the contacts 222 of the cartridge 34 contact the contacts 220 of the channel 22. Depending on the contact pattern on the cartridge 34, different resistors may be in the completed circuit. The resistors may be connected to the control circuit 135, and may be used in the RC circuits to generate the timing signals for the switches 146, 140a, 140b. That way, the control circuit 135 can control the switches 146, 140a-b based on the type of cartridge 34 loaded in the end effector 12.

In another embodiment, the lower surface of the cartridge 34 may comprise a plunger 230, as shown in FIG. 22. The channel 22 may comprise a number of switches 232, as shown in FIG. 23, one of which is actuated by the plunger 230 when the cartridge 34 is loaded in the end effector 12. The switch 232 may have a different associated resistor circuit. Each of the resistor circuits may be connected to the control circuit 135, but only one would be activated when the cartridge 34 is loaded in the channel 22, depending on the location of the plunger 230. Each replaceable cartridge 34 having the same cut length preferably would have the plunger 230 in the same position. Cartridges 34 with different lengths would preferably have plungers 230 in different positions. Because the end effector 12 may only accommodate a finite number of different cartridges (e.g., 5), the channel 22 would only need a corresponding number of switches 232 and there would only be a corresponding number of acceptable plunger locations.

Figure 24:
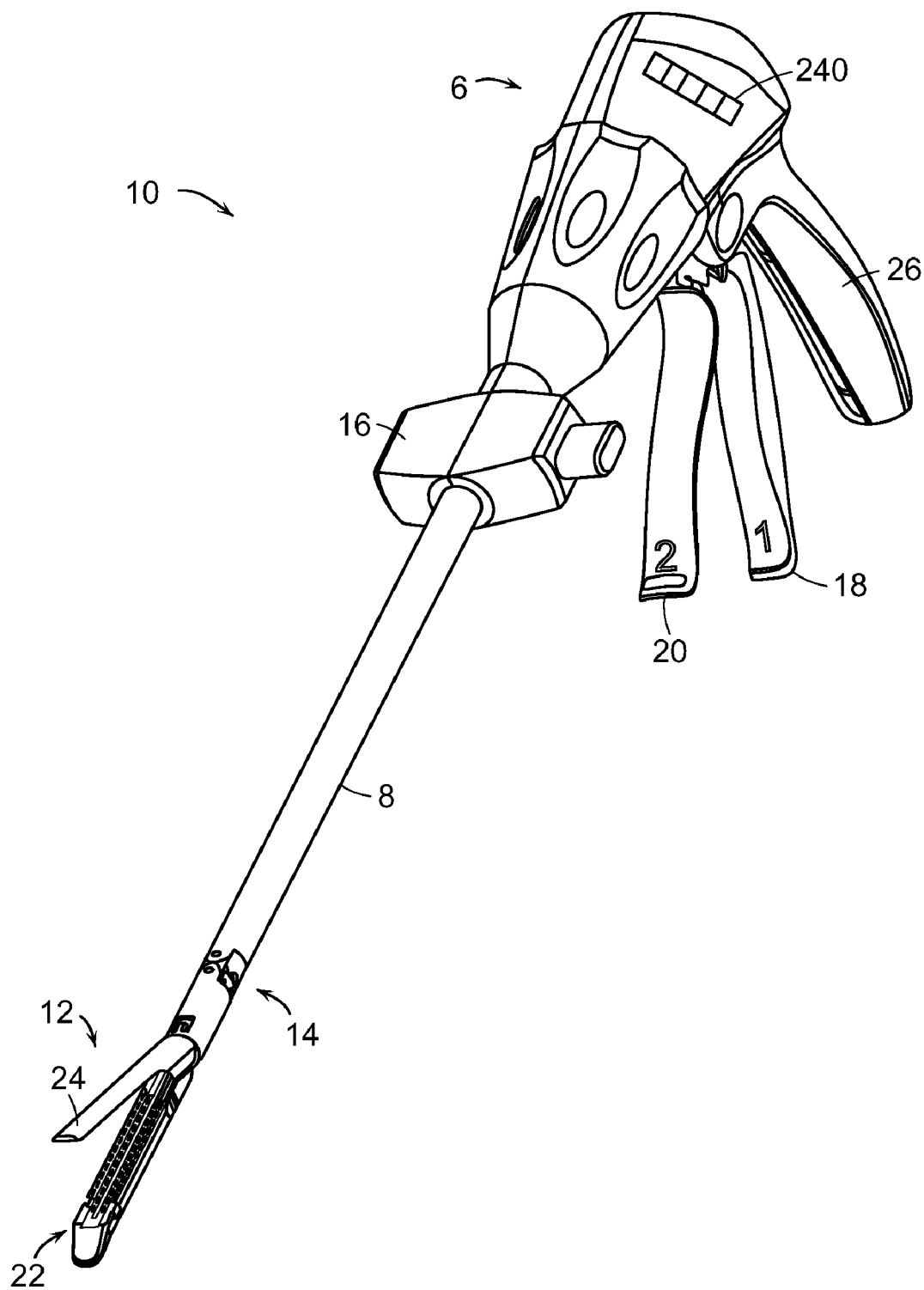

In other embodiments, the instrument 10 may comprise an external selector 240, such as dip switch or other suitable input device, whereby an operator of the instrument or other person could input identifying data for the cartridge 34 being used. As shown in FIG. 24, the handle may comprise such a selector 240 for embodiments where the control circuit 135 comprises an IC or embodiments where the control circuit 135 does not comprise any ICs.

Figure 25:
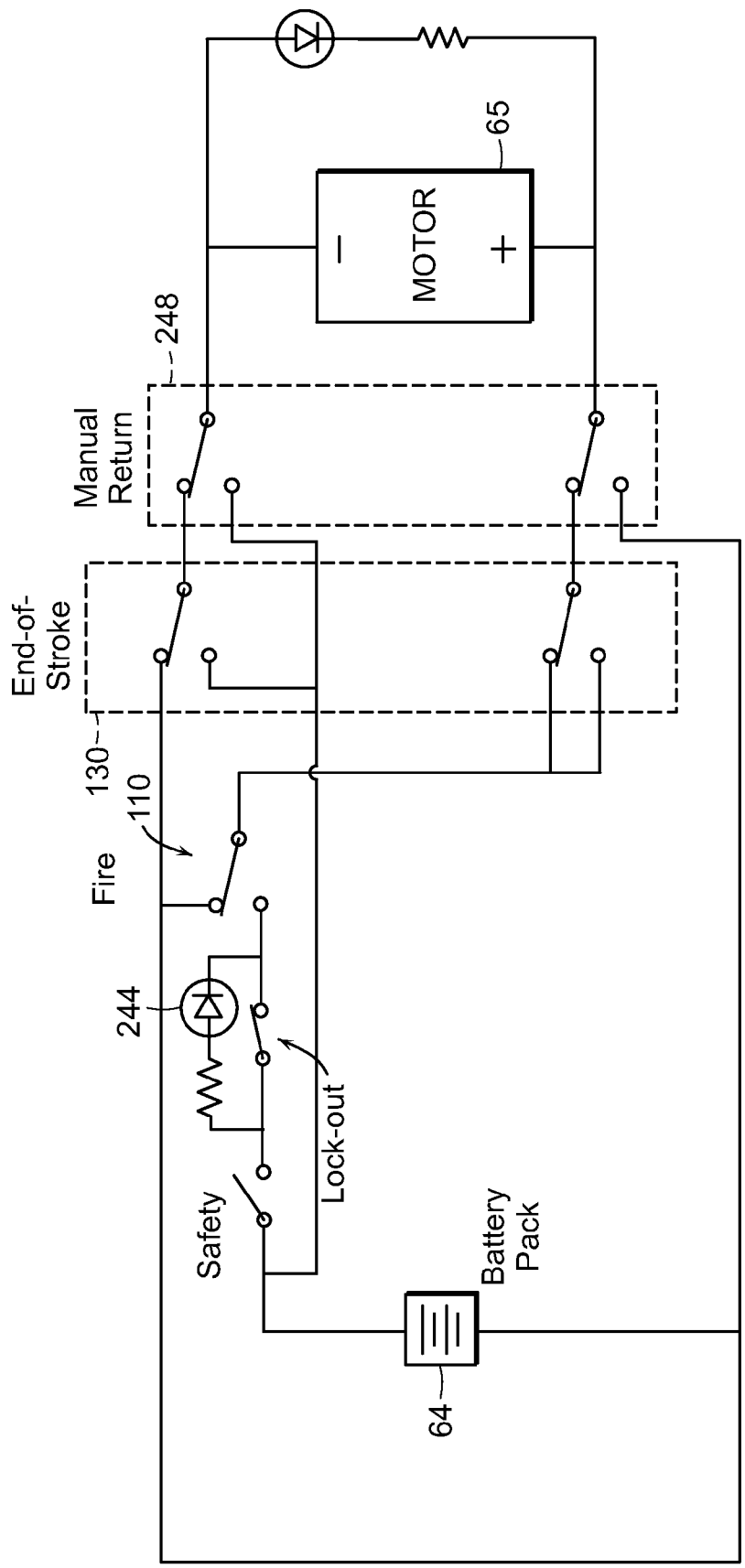

FIG. 25 shows another embodiment of the motor circuit. When the run motor (or fire) switch 110 is closed (it is shown in an open state in FIG. 25), when the safety switch 240 is closed (it is shown open in FIG. 25) indicating that the device safety is set, and when the normally-closed lockout switch 242 it opened indicating that the instrument is not in a lockout condition, current flows through the safety switch 240, through the lockout indicator 244 (which may be a LED as shown in FIG. 25) to the motor 65. When the end of the cutting stroke is reached, the end-of-stroke or direction switch 130 is switched, reversing the direction of the motor 65 (with the fire switch 110 also having been released). In this state, current also flows through a reverse direction indicator 246, such as an LED, providing a visual indication that the motor direction has been reversed.

As shown in FIG. 25, the circuit may also comprise a manual return switch 248. The operator may manually flip this switch if the cutting instrument 32 has only been partially fired. Switching the manual return switch 248 causes the motor 65 to reverse rotate, causing the cutting instrument 32 to return to its original or home position.

The battery 64 of the instrument 10 may comprise one or more series-connected battery cells. In various embodiments, a cell selection switch may control how many of the battery cells are being used to power the motor 65 at a given time to control the power available to the motor 65. This would allow the operator of the instrument to have greater control over both the speed and the power of the motor 65. In another embodiment, the instrument may comprise a power regulator, including, for example, a DC-to-DC converter, that regulates the voltage supplied to the motor. Further, the voltage set point for the power regulator could be set so that the voltage delivered from the power source is less than the voltage at which the power source delivers maximum power. That way, the power source (e.g., a number of series-connected battery cells) could operate on the "left" or increasing side of the power curve, so that increases in power would be available.

In addition, according to various embodiments, the power source 64 may comprise secondary accumulator devices, such as rechargeable batteries or supercapacitors. Such secondary accumulator devices may be charged repeatedly by replaceable batteries. A charge management circuit may control the charging of the secondary accumulator devices and provide various status signals, such as an alert, when the charging of the secondary accumulator devices is complete.

In other embodiments, the power source or power pack comprising the secondary accumulator devices may be removable from the instrument and connectable to a remote charger base. The charger base may charge the secondary accumulator devices, such as from the AC electrical mains or a battery. The charger base may also comprise a processor and memory unit. Data stored in a memory of the removable power pack may be downloaded to the charger base, from which it may be uploaded for later use and analysis, such as by the user (e.g., physician), the manufacturer, or distributor of the instrument, etc. The data may comprise operating parameters, such as charge cycle information, as well as ID values for various replaceable components of the instrument, such as the staple cartridge.

More details regarding such power sources may be found in commonly assigned U.S. application Ser. No. 12/031,556, entitled "Motorized surgical cutting and fastening instrument," and Ser. No. 12/031,567, entitled "Motorized surgical cutting and fastening instrument having handle based power source,", both of which were filed on Feb. 14, 2008, and both of which are incorporated herein by reference in their entirety.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a thermoformed plastic shell covered with a sheet of TYVEK. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam and other methods.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A surgical cutting and fastening instrument comprising:
an end effector comprising a cutting instrument that, when actuated, longitudinally traverses the end effector along a cutting travel path to cut tissue clamped in the end effector, wherein the cutting travel path has an initial position at a beginning of the cutting travel path and an end-of-stroke position at an end of the cutting travel path;
a cutting instrument position sensor that senses a position of the cutting instrument in the end effector along the cutting travel path;
a shaft connected at its distal end to the end effector; and
a handle connected to a proximate end of the shaft, wherein the handle comprises:
an electric motor for actuating the cutting instrument;
a motor control circuit for controlling the motor, wherein the motor control circuit comprises:
a power source connected to the motor for electrically powering the motor; and
a current control circuit, connected to the power source, for varying the current supplied to the motor from the power source, wherein the current control circuit controls the motor according to a switching architecture and based on a position of the cutting instrument along the cutting travel path relative to the end-of-stroke position and the initial position, as sensed by the cutting instrument position sensor, wherein the switching architecture comprises:
a first, low power operational mode for a first portion of a cutting travel path of the cutting instrument when the cutting instrument is within a first non-zero threshold distance along the cutting travel path from the initial position; and
a second, high power operational mode for a second portion the cutting travel path of the cutting instrument when the cutting instrument is between the first non-zero threshold distance and a second non-zero threshold distance from the initial position of the cutting travel path, wherein the first non-zero threshold distance is less than the second non-zero threshold distance, and where greater current is supplied to the motor during the second, higher power operational mode than during the first, low power operational mode.

2. The surgical cutting and fastening instrument of claim 1, wherein the current control circuit comprises:
a switch connected to the power source;
a resistor connected in parallel with the switch; and
a control circuit for controlling the switch.

3. The surgical cutting and fastening instrument of claim 1, wherein the current control circuit comprises a variable resistor.

4. The surgical cutting and fastening instrument of claim 1, wherein the current control circuit comprises a pulse width modulation control circuit.

5. The surgical cutting and fastening instrument of claim 1, wherein the current control circuit comprises a frequency modulation control circuit.

6. The surgical cutting and fastening instrument of claim 1, wherein the current control circuit comprises an amplifier circuit.

7. The surgical cutting and fastening instrument of claim 1, wherein:
the cutting instrument has a return travel path that follows the cutting travel path, wherein the return travel path begins at the end-of-stroke position and ends at the initial position; and
the switching architecture of the current control circuit reverses a rotational direction of the motor for the return travel path when the cutting instrument reaches the end-of-stroke position.

8. The surgical cutting and fastening instrument of claim 7, wherein the switching architecture of the current control circuit removes current from the motor on the cutting travel path when the cutting instrument is within the second non-zero threshold distance from the initial position.

9. The surgical cutting and fastening instrument of claim 8, wherein the switching architecture of the current control circuit removes current from the motor along the return travel path of the cutting instrument prior to the cutting instrument reaching the initial position.

10. The surgical cutting and fastening instrument of claim 9, wherein the motor control circuit does not include an integrated circuit.

11. The surgical cutting and fastening instrument of claim 7, wherein the switching architecture of the current control circuit reverts to the first, low power operational mode when the cutting instrument is within the second non-zero threshold distance from the initial position.

12. The surgical cutting and fastening instrument of claim 7, wherein the switching architecture comprises a third operational mode for when the cutting instrument is farther than the second non-zero threshold distance from the initial position, wherein greater current is supplied to the motor during the second, higher power operational mode than during the third operational mode, and the current supplied to the motor during the first, low power operational mode is different from the current supplied to the motor during the third operational mode.

13. The surgical cutting and fastening instrument of claim 1, wherein the motor control circuit does not include an integrated circuit.

14. The surgical cutting and fastening instrument of claim 1, wherein the motor control circuit further comprises an indicator for visually indicating a rotational direction of the motor.

15. The surgical cutting and fastening instrument of claim 1, wherein the motor control circuit further comprises a manual return switch which, when activated, causes the motor to reverse rotate.

16. The surgical cutting and fastening instrument of claims 1, wherein:
the motor comprises a DC motor; and
the power source comprises a DC power source.

17. The surgical cutting and fastening instrument of claim 1, wherein the cutting instrument position sensor indirectly senses the position of the cutting instrument in the end effector.

* * * * *